United States Patent
Davis et al.

(10) Patent No.: US 11,707,631 B2
(45) Date of Patent: *Jul. 25, 2023

(54) ANTENNA ASSEMBLIES FOR USE WITH TRANSCUTANEOUSLY POWERED MEDICAL IMPLANTS

(71) Applicant: ADVANCED BIONICS AG, Staefa (CH)

(72) Inventors: Austin Charles Davis, Simi Valley, CA (US); James George Elcoate Smith, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 14 days.

This patent is subject to a terminal disclaimer.

(21) Appl. No.: 17/511,807

(22) Filed: Oct. 27, 2021

(65) Prior Publication Data

US 2022/0047875 A1 Feb. 17, 2022

Related U.S. Application Data

(63) Continuation of application No. 16/027,220, filed on Jul. 3, 2018, now Pat. No. 11,185,702.

(60) Provisional application No. 62/530,423, filed on Jul. 10, 2017, provisional application No. 62/530,413, filed on Jul. 10, 2017.

(51) Int. Cl.
| | | |
|---|---|---|
| A61N 1/372 | (2006.01) | |
| A61N 1/375 | (2006.01) | |
| H04B 5/00 | (2006.01) | |
| A61N 1/378 | (2006.01) | |
| H01Q 7/00 | (2006.01) | |
| A61N 1/36 | (2006.01) | |
| H01Q 1/27 | (2006.01) | |
| H01Q 1/36 | (2006.01) | |

(52) U.S. Cl.
CPC ..... *A61N 1/37229* (2013.01); *A61N 1/36038* (2017.08); *A61N 1/375* (2013.01); *A61N 1/3787* (2013.01); *H01Q 1/273* (2013.01); *H01Q 7/00* (2013.01); *H04B 5/00* (2013.01); *H01Q 1/36* (2013.01)

(58) Field of Classification Search
CPC ............ A61N 1/37229; A61N 1/36038; A61N 1/375; A61N 1/3787; H01Q 1/273; H01Q 7/00; H04B 5/00
See application file for complete search history.

(56) References Cited

U.S. PATENT DOCUMENTS

| | | |
|---|---|---|
| 3,753,203 A | 8/1973 | Link |
| 3,870,987 A | 3/1975 | Wiley et al. |

(Continued)

FOREIGN PATENT DOCUMENTS

| | | |
|---|---|---|
| WO | WO 2012/047550 A1 | 4/2012 |
| WO | WO 2015021359 A1 | 2/2015 |

(Continued)

OTHER PUBLICATIONS

Litz wire. In Wikipedia. Retrieved Apr. 17, 2015, from https://en.wikipedia.org/wiki/Litz_wire.

(Continued)

*Primary Examiner* — Mallika D Fairchild
(74) *Attorney, Agent, or Firm* — Henricks Slavin LLP

(57) ABSTRACT

An antenna assembly for use with a medical implant includes an antenna that defines at least one turn and an electromagnetic shield.

16 Claims, 19 Drawing Sheets

(56) References Cited

U.S. PATENT DOCUMENTS

| | | |
|---|---|---|
| 5,385,578 A | 1/1995 | Bush et al. |
| 5,876,326 A | 3/1999 | Takamura et al. |
| 6,515,632 B1 | 2/2003 | McLean |
| 6,542,777 B1 | 4/2003 | Griffith et al. |
| 7,191,007 B2 | 3/2007 | Desai et al. |
| 7,876,282 B2 | 1/2011 | Keilman et al. |
| 8,781,606 B2 | 7/2014 | Keilman et al. |
| 8,825,171 B1 | 9/2014 | Thenuwara et al. |
| 10,543,369 B2 | 1/2020 | Nyberg, II et al. |
| 11,185,702 B2 | 11/2021 | Davis et al. |
| 2005/0134519 A1 | 6/2005 | Fukano et al. |
| 2006/0038730 A1 | 2/2006 | Parsche |
| 2008/0051854 A1 | 2/2008 | Bulkes et al. |
| 2009/0248105 A1 | 10/2009 | Keilman et al. |
| 2010/0046779 A1 | 2/2010 | Crawford et al. |
| 2011/0009925 A1 | 1/2011 | Leigh et al. |
| 2012/0089202 A1 | 4/2012 | Staller |
| 2014/0197832 A1 | 7/2014 | Driesel et al. |
| 2014/0314264 A1 | 10/2014 | Meskens et al. |
| 2015/0025613 A1* | 1/2015 | Nyberg, II ......... A61N 1/37229 29/601 |
| 2018/0071542 A1 | 3/2018 | Nyberg, II et al. |
| 2019/0009096 A1 | 1/2019 | Davis et al. |
| 2019/0334230 A1 | 10/2019 | Jesme et al. |
| 2021/0234265 A1 | 7/2021 | Smith et al. |

FOREIGN PATENT DOCUMENTS

| | | |
|---|---|---|
| WO | WO 2016171833 A1 | 10/2016 |
| WO | WO 2016198426 A1 | 12/2016 |
| WO | WO 2017218619 A1 | 12/2017 |

OTHER PUBLICATIONS

Litz Wire Types and Constructions. Retrieved Apr. 17, 2015, from www.newenglandwire.com.
Schaffer. General Characteristics of DFT® Composite Wire. Fort Wayne Metals Research Products Corporation. 2002.

* cited by examiner

ANTENNA ASSEMBLIES FOR USE WITH TRANSCUTANEOUSLY POWERED MEDICAL IMPLANTS

CROSS-REFERENCE TO RELATED APPLICATIONS

This application is continuation of U.S. application Ser. No. 16/027,220, filed Jul. 3, 2018, now U.S. Pat. No. 11,185,702, which claims the benefit of U.S. Provisional Application No. 62/530,413, filed Jul. 10, 2017, which is incorporated herein by reference, and also claims the benefit of U.S. Provisional Application No. 62/530,423, filed Jul. 10, 2017, which is incorporated herein by reference.

BACKGROUND

1. Field

The present disclosure relates generally to transcutaneously powered medical implants.

2. Description of the Related Art

Inductive links are commonly used to transmit power and data to implanted medical devices such as, for example, prosthetic devices including cochlear implants and retinal implants, cardiac pacemakers, implantable defibrillators, recording devices, and neuromuscular stimulators. The implanted devices include (or are connected to) an internal antenna coil, and an external antenna coil is positioned over the internal antenna coil. Power and in some instances data is supplied to the implanted devices by way of the inductive link between the antenna coils.

In the exemplary context of implantable cochlear stimulation ("ICS") systems, which include an external sound processor as well as a cochlear implant with an electrode array within the cochlea, the external antenna coil may be carried by a headpiece that is connected to the external sound processor. The sound processor transmits power and stimulation data (e.g., a pulse sequence having varying pulse widths and/or amplitudes) through a power modulation scheme to the antenna coil of the cochlear implant by way of an inductive link. One conventional implant antenna coil is a three turn inductor that includes a conductor within a non-conductive carrier. The conductor includes biocompatible multi-wire metal cables formed from gold, platinum or titanium wire. Electrical stimulation current is then applied to varying electrode combinations in the electrode array to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics Harmony™ BTE sound processor, the Advanced Bionics Naida CI Q Series BTE sound processors and the Advanced Bionics Neptune™ body worn sound processor.

In some instances, an electromagnetic shield is formed around the antenna coil in order to reduce noise and undesirable alteration of the characteristics of the antenna coil caused by external objects. One exemplary method of forming an electromagnetic shield involves, among other things, overmolding a silicone shield guide onto the antenna coil, then piercing the molded shield guide at two locations, anchoring a shield wire (such as a platinum wire) at the pierced locations, and carefully wrapping the shield wire around the mold (and antenna coil). The present inventors have determined that the wrapped wire shield is susceptible to improvement. For example, the present inventors have determined that, in addition to being time consuming and expensive, the associated manufacturing process does not produce consistent results. As such, reworking of completed wrapped wire shields is frequently required.

SUMMARY

An antenna assembly for use with a medical implant includes an antenna that defines at least one turn and an electromagnetic shield with a first shield portion that defines an interior volume with an open end and in which the antenna is located, and a second shield portion, configured to cover the open end of the first shield portion, that is secured to the first shield portion. The present inventions also include implantable medical devices, such as cochlear implants, with such an antenna assembly.

A method includes the steps of positioning an implantable medical device antenna that defines at least one turn in a first shield portion that defines an interior volume with an open end, and positioning a second shield portion over the open end of the first shield portion.

An antenna assembly for use with a medical implant includes an antenna that defines at least one turn and an electromagnetic shield assembly wrapped around antenna having an electrically non-conductive flexible shield carrier and an electromagnetic shield carried by the flexible shield carrier. The present inventions also include implantable medical devices, such as cochlear implants, with such an antenna assembly.

A method includes the step of wrapping an electromagnetic shield assembly, including an electrically non-conductive flexible shield carrier and an electromagnetic shield carried by the flexible shield carrier, around an implantable medical device antenna to form an annularly shaped antenna assembly.

An antenna assembly for use with a medical implant an antenna that defines at least one turn and an electromagnetic shield that forms a discontinuous loop around the antenna.

A method includes the steps of deforming at least a portion of an electromagnetic shield with a pre-set overall annular shape in such a manner that a perimeter opening of the electromagnetic shield is enlarged, and inserting a portion of a medical implant antenna defining at least one turn into the deformed portion of the electromagnetic shield by way of the enlarged perimeter opening.

There are a number of advantages associated with such apparatus and methods. For example, the apparatus and methods simplify and standardize the process of assembling an antenna assembly, thereby reducing the time and expense associated therewith (as compared to conventional methods), and also reduce rework.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of systems including, but not limited to, those that provide sound (i.e., either sound or a perception of sound) to the hearing impaired. One example of such a system is an ICS system where an external sound processor communicates with a cochlear implant and, accordingly, the present inventions may be discussed in the context of cochlear implants. The present inventions are not, however, so limited, and have application in other systems where, for example, power and data are transmitted to an implanted medical device by way of an inductive link.

Figure 1:
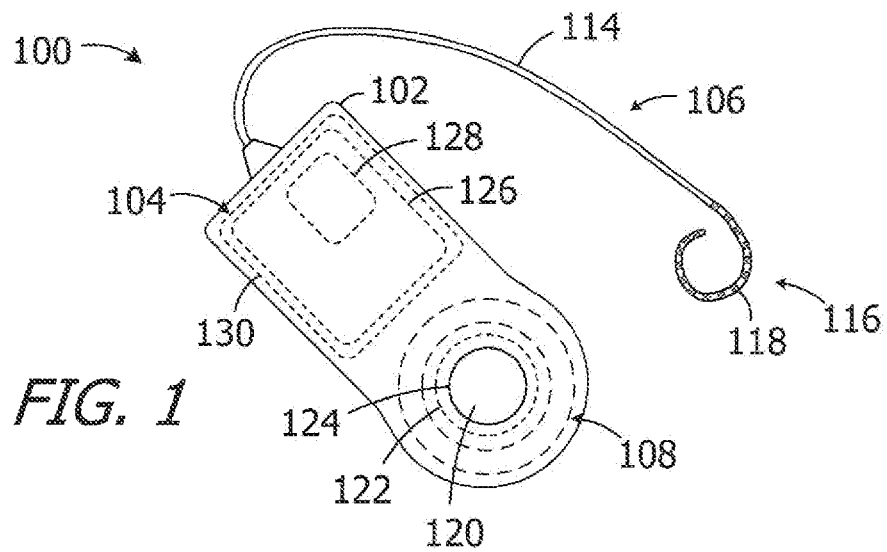
FIG. 1 is a top view of an exemplary implantable cochlear stimulator in accordance with one embodiment of a present invention.
Figure 2:
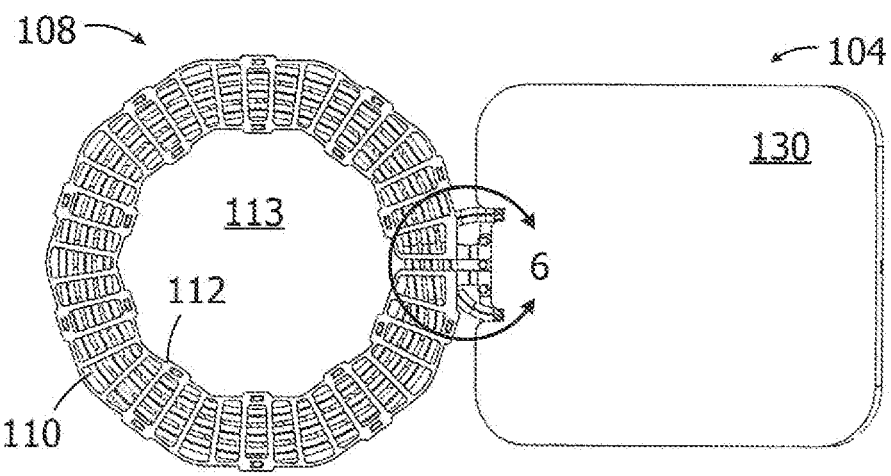
FIG. 2 is a bottom view of a portion of the implantable cochlear stimulator illustrated in FIG. 1.

One example of a cochlear implant (or "implantable cochlear stimulator") is the cochlear implant 100 illustrated in FIGS. 1 and 2. The cochlear implant 100 includes a flexible housing 102 formed from a silicone elastomer or other suitable material, a processor assembly 104, a cochlear lead 106, and an antenna assembly 108 with an antenna coil (or "antenna") 110 and an electromagnetic shield (or "shield") 112. The antenna 110 may be used to receive data and power by way of an external antenna that is associated with, for example, a sound processor unit, while the electromagnetic shield 112 functions in a manner similar to the electromagnetic shields in other hearing related devices. The cochlear lead 106 may include a flexible body 114, an electrode array 116 at one end of the flexible body, and a plurality of wires (not shown) that extend through the flexible body from the electrodes 118 (e.g., platinum electrodes) in the array 116 to the other end of the flexible body. A magnet 120 is located within a region encircled by the antenna assembly 108 (e.g., within an internal pocket 122 defined by the housing 102). The magnet 120 ensures that an external antenna will be properly positioned relative to the antenna 110. The antenna assembly 108, as well as the other antenna assemblies described below, have an overall annular shape with an open central region 113 to accommodate the magnet 120 and magnet pocket 122. An opening 124 allows the magnet 120 to be removed from the internal pocket 122 if necessary. The exemplary processor assembly 104, which is connected to the electrode array 116 and antenna 110, includes a printed circuit board 126 with a stimulation processor 128 that is located within a hermetically sealed case 130. The case 130 may be formed from titanium or other suitable materials. The stimulation processor 128 converts the stimulation data into stimulation signals that are transmitted to the cochlea by way of the electrodes 118 of the electrode array 116.

Figure 3:
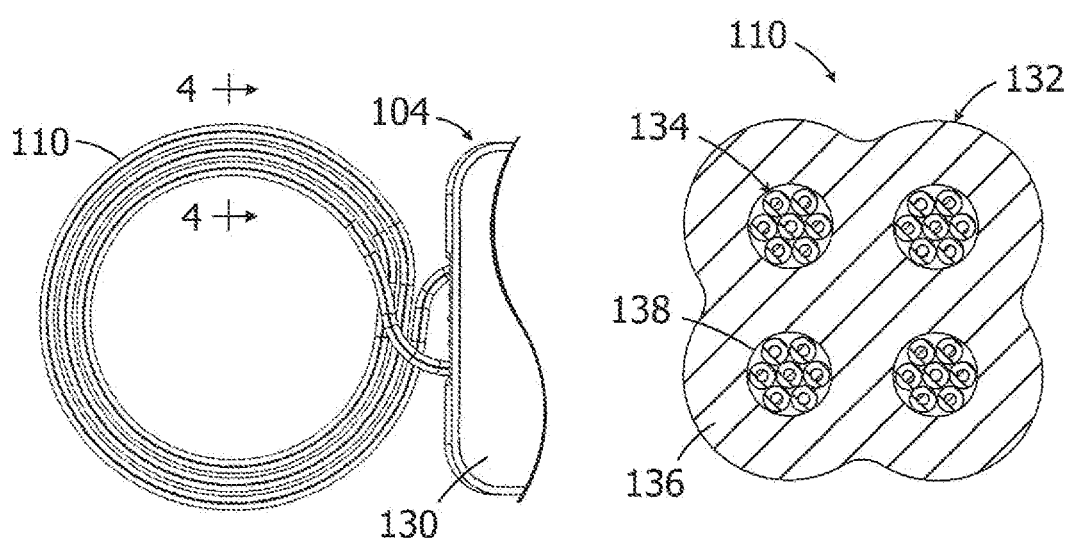
FIG. 3 is a top view of a portion of the implantable cochlear stimulator illustrated in FIG. 1.
Figure 4:
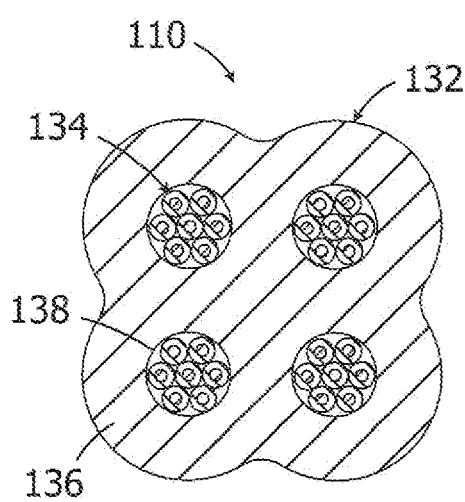
FIG. 4 is a section view of a single turn taken along line 4-4 in FIG. 3.
Figure 5:
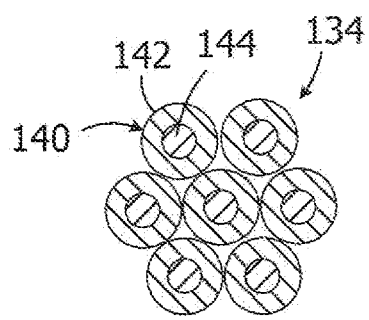
FIG. 5 is a section view of an exemplary conductor.

Referring to FIGS. 3-5, the exemplary antenna 110 is formed by an inductor assembly 132 that includes one or more metallic conductors 134. The metallic conductors are located within a carrier 136 that maintains the positon of the metallic conductors relative to one another. The inductor assembly 132 defines one or more turns (or "loops" or "windings"), the number of which is determined by the intended application, and there are three turns in the illustrated embodiment. The exemplary carrier 136 includes a lumen 138 for each one of the metallic conductors 134. The carrier 136 may be formed from a dense elastomeric electrically non-conductive material such as silicone rubber. Turning to FIG. 5, the conductors 134 may be in the form of multi-wire cables (sometimes referred to as "Litz wires"), and each wire 140 may be a drawn filled tubing ("DFT") that includes an outer tube 142 (e.g., an MP35N® nickel alloy tube) filled with an inner core 144 (e.g., a silver or silver alloy core). DFT is a registered trademark of Fort Wayne Metals Research Products Corp. and MP35N is a registered trademark of SPS Technologies. In the illustrated embodiment, the conductors 134 include seven wires 140 that are arranged in a hexagonal formation where six of the wires are twisted around a center wire. The ends of the metallic conductors 134 are exposed (FIG. 6) so as to facilitate connection to the circuitry within the processor assembly 104.

The exemplary antennas 110 and 110a (below) are also sized for use in a cochlear implant. As such, the outer diameter of the antennas 110 and 110a may be from 15 mm to 30 mm. In other implantable medical device applications, the antenna diameter may be from 5 mm to 15 mm.

Figure 6:
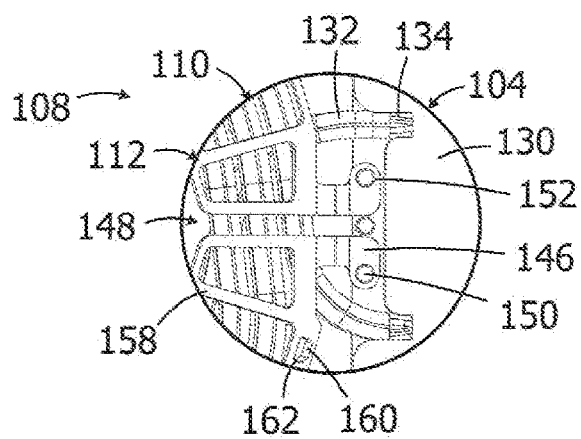
FIG. 6 is an enlarged view of a portion of FIG. 2.

As illustrated in FIG. 6, the exemplary shield 112 includes a pair of connector tabs 146 that are located on opposite sides of a gap 148. The shield tabs 146 are connected to the titanium case 130, and the case is connected to ground circuitry within the case. In the illustrated implementation, the case 130 includes a pair of alignment posts 150 that orient shield 112 relative to the case, the tabs 146 include alignment apertures 152 through which the posts extend, and the tabs are welded to the case.

Figure 7:
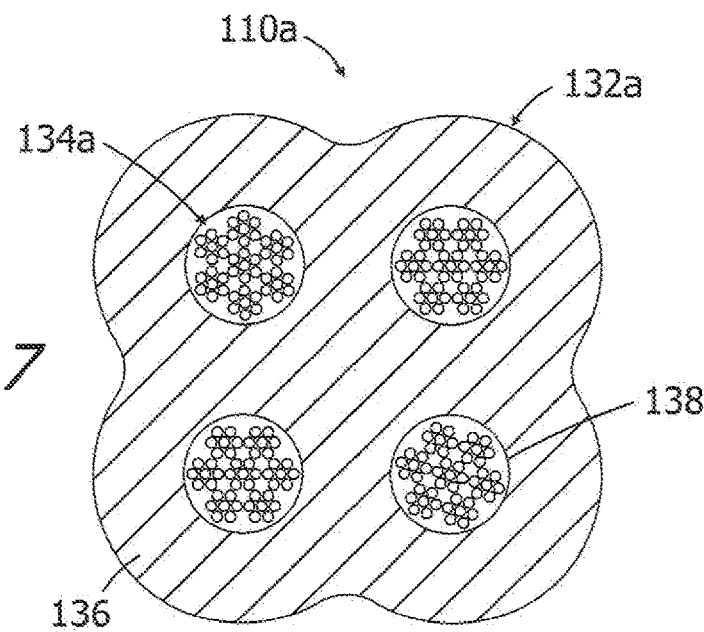
FIG. 7 is a section view of a portion of an exemplary inductor assembly.
Figure 8:
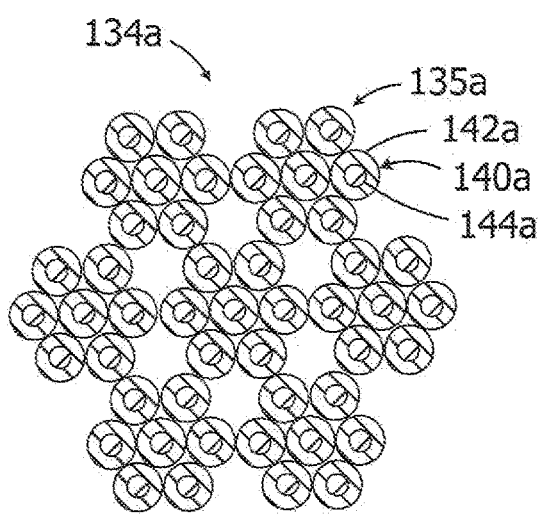
FIG. 8 is a section view of an exemplary inductor.
Figure 9:
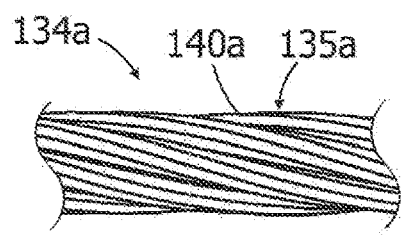
FIG. 9 is a side view of an exemplary inductor.

Another exemplary antenna, which may be employed in place of the antenna 110, is generally represented by reference numeral 110a in FIG. 7 and similar elements are represented by similar reference numerals. The antenna 110a includes an inductor assembly 132a with a plurality of conductors 134a (FIGS. 8 and 9). Each conductor 134a may be formed from a plurality of multi-wire cables 135a. Each wire 140a in the cables 135a may be in the form of DFT with an outer tube 142a and an inner core 144a. In the illustrated embodiment, the conductors 134a include seven multi-wire cables 135a that are arranged in a hexagonal formation where six of the cables 135a are twisted around a center cable, and each cable 135a include seven wires 140a arranged in a hexagonal formation where six of the wires are twisted around a center wire. Additional information concerning the antenna 110a may be found in WO Pub. No. 2016/171833, which is incorporated herein by reference in its entirety.

Figure 10:
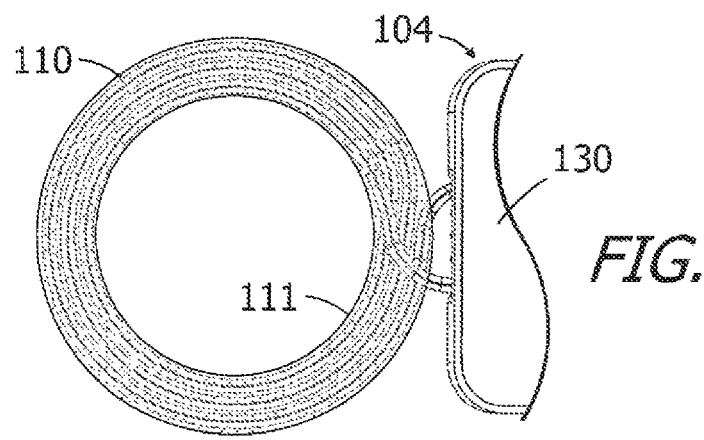
FIG. 10 is a top view of a portion of an implantable cochlear stimulator.

There may be some instances where an antenna 110 (or 110a) will not self-maintain the three concentric loops shape illustrated in FIG. 3 or other desired shape. One exemplary method of maintaining the antenna in the desired shape involves overmolding an antenna holder 111 (FIG. 10), which may be formed from silicone or other suitable materials, onto the antenna 110 (or 110a). The antenna holder 111 will be positioned within the shield 112 along with the antenna 110 during the assembly process. Other instrumentalities and methods for maintaining antenna shape are described below with reference to FIGS. 18-21 and 25-30A.

Figure 11:
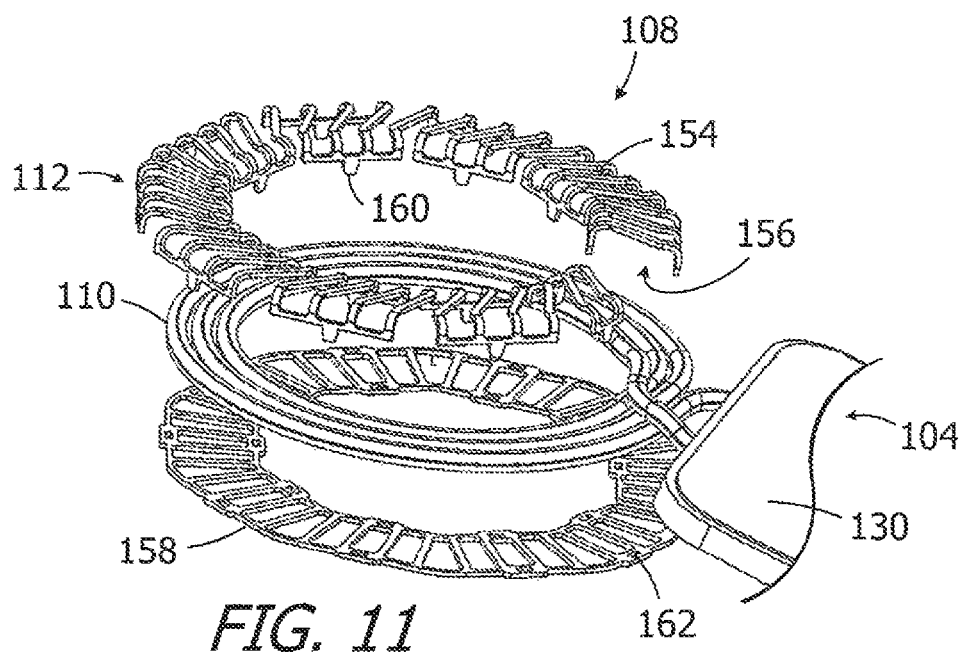
FIG. 11 is a partially exploded perspective view of a portion of the implantable cochlear stimulator illustrated in FIG. 1.

Turning to FIG. 11, the exemplary shield 112 is a two-piece cage-like structure that extends around the antenna 110. The shield 112 includes a first shield portion 154 that defines an interior volume 156 for the antenna 110 and a second shield portion 158 that covers the open end of the interior volume. The first and second shield portions 154 and 158 are separate structures that are secured to one another during the assembly process. At least one of the first and second shield portions 154 and 158 includes alignment apparatus that is configured to align the first and second shield portions with one another as the first and second shield portions are brought into contact with one another during assembly of the shield. In the illustrated embodiment, the first and second shield portions 154 and 158 also respectively include one or more alignment tabs 160 and one or more apertures 162 that orient the first and second shield portions relative to one another. The first and second shield portions 154 and 158 may be welded (or crimped, soldered, or brazed) to one another at the tab 160/aperture 162 locations during the assembly process, or at other locations around the inner and/or outer perimeters of the shield 112, as is described below with reference to FIG. 29. Biocompatible conductive epoxy may also be used to secure the shield portions 154 and 158 to one another. In other implementations, apertures may be located on the first shield portion 154 and tabs may be located on the second shield portion. It should also be noted here that the tabs 160 may be slightly smaller than the apertures 162 (as shown), or slightly larger to ensure a tight fit.

Figure 12:
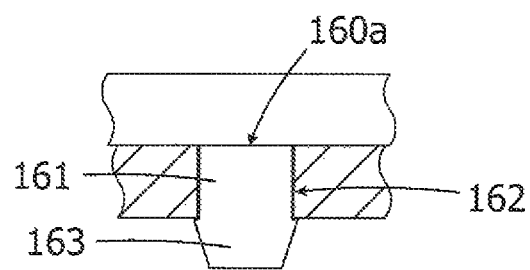
FIG. 12 is a side, partial section view of an exemplary shield latch.
Figure 13:
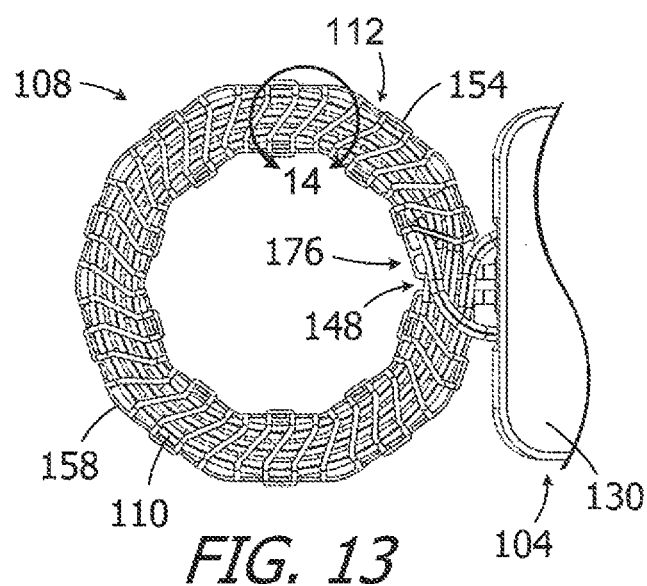
FIG. 13 is a top view of a portion of the implantable cochlear stimulator illustrated in FIG. 1.
Figure 14:
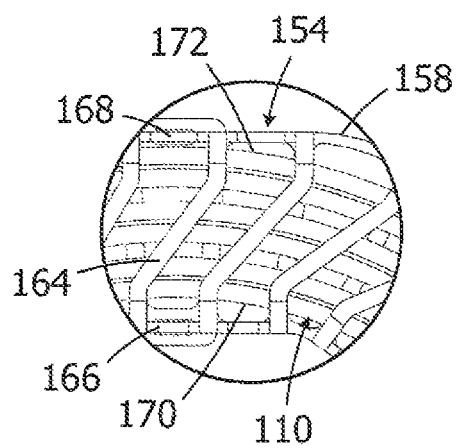
FIG. 14 is an enlarged view of a portion of FIG. 13.
Figure 15:
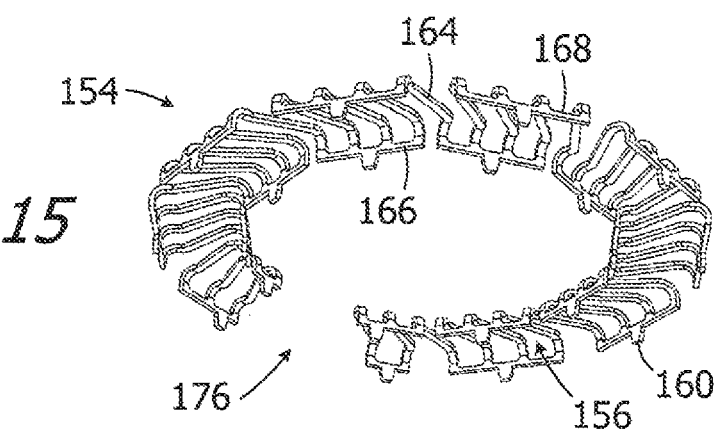
FIG. 15 is a perspective view of a portion of the implantable cochlear stimulator illustrated in FIG. 1.
Figure 16:
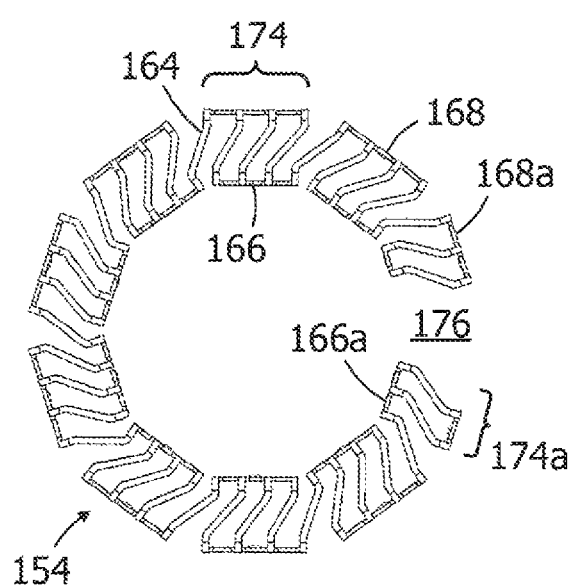
FIG. 16 is a top view of a portion of the implantable cochlear stimulator illustrated in FIG. 1.
Figure 17:
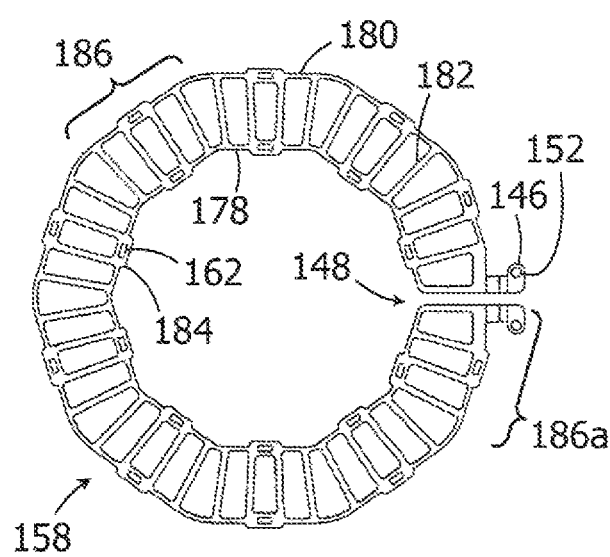
FIG. 17 is a top view of a portion of the implantable cochlear stimulator illustrated in FIG. 1.
Figure 18:
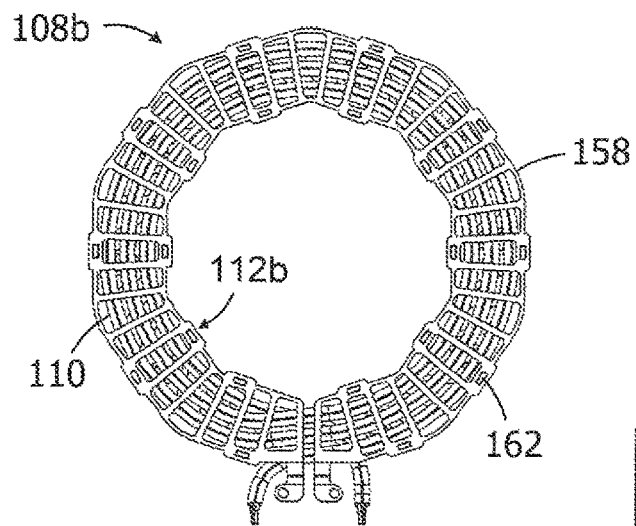
FIG. 18 is a bottom view of an antenna assembly in accordance with one embodiment of a present invention.
Figure 19:
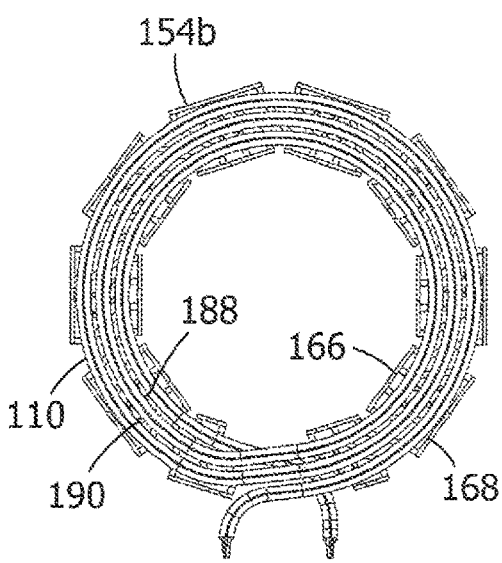
FIG. 19 is a bottom view of a portion antenna assembly illustrated in FIG. 18.
Figure 20:
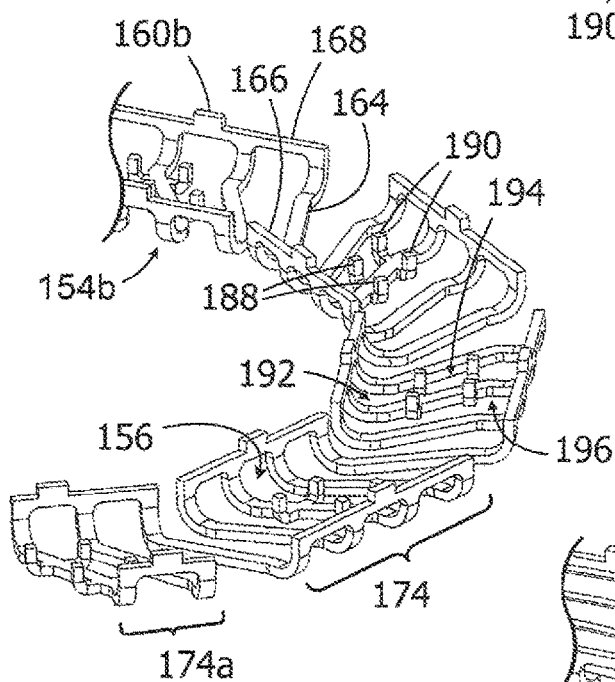
FIG. 20 is a perspective view of a portion antenna assembly illustrated in FIG. 18.
Figure 21:
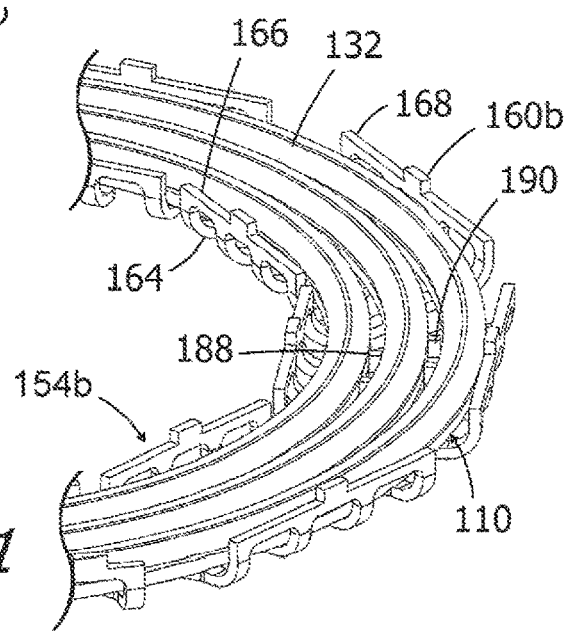
FIG. 21 is a perspective view of a portion antenna assembly illustrated in FIG. 18.

In other instances, the tabs and apertures may be configured such that, in addition to being properly aligned, the first and second shield portions 154 and 158 will be mechanically connected to one another when they are brought together. Any suitable instrumentality that secures the shield portions to one another may be employed. By way of example, and referring to FIG. 12, the exemplary tab 160a (which may be employed in place of tabs 160) includes a relatively narrow portion 161 and a tapered latch 163 that mechanically interconnects with the second shield portion 158 after passing through the aperture 160.

In those instances where an overmolded antenna holder 111 is employed, the outer surface of the antenna holder may include protrusions and indentations (not shown) that will align the first and second shield portions 154 and 158 with one another.

Referring to FIGS. 13-17, the first portion 154 of the exemplary shield 112 includes a plurality of spaced apart arch-shaped members 164 that are connected to inner and outer base members 166 and 168. The arch-shaped members 164 extend across the associated portions of the antenna 110, from the inner edge 170 to the outer edge 172, while the base members 166 extend in a direction that is tangential to the associated portion of the antenna. In the illustrated implementation, the arch-shaped members 164 and base members 166/168 are arranged in groups 174 that include five arch-shaped members, although some of the arch-shaped members are shared. One arch-shaped member 164 in each group is connected to the base member 166 of one adjacent group, while another arch-shaped member 164 in each group 174 is connected to the base member 168 of the other adjacent group. The end groups 174a, which may include fewer arch-shaped members 164 and shorter inner and outer base members 166a and 168a, are each connected to a single group 174 and define a gap 176 therebetween.

The second portion 158 of the exemplary shield 112 includes inner and outer base members 178 and 180 as well as a plurality of flat members 182 that extend from the inner base member to the outer base member. The apertures 162 are located in the thickened regions 184 of the inner and outer base members 178 and 180. In the illustrated implementation, the flat members 182 are arranged in groups 186 that include four flat members. The end groups 186a, which are located on opposite sides of the gap 148, include only three flat members 182.

The respective configurations of the first and second shield portions 154 and 158 are such that when the first and second shield portions are brought together, the inner and outer base members 166 and 168 of the first shield portion will be aligned with the inner and outer base members 178 and 180. In other implementations, the inner diameter of the first shield portion (as defined by the inner base members 166) will be greater than the inner diameter of the second shield portion (as defined by the inner base member 178) and the inner tabs 160 and apertures will be omitted. Here, there will a discontinuity (or gap) in the shield between the inner base members 166 and the inner base member 178.

As alluded to above, the present antenna assemblies include those with shields that are configured to assist in the formation of the loops of the associated antenna and to maintain the antenna in the desired shape. To that end, and turning to FIGS. 18-21, the exemplary antenna assembly 108b is substantially similar to antenna assembly 108 and similar elements are represented by similar reference numerals. For example, the antenna assembly 108b includes an antenna 110 and an electromagnetic shield (or "shield") 112b that is essentially identical to the shield 112. The shield 112b has, for example, a first shield portion 154b that defines an interior volume 156 for the antenna 110 and a second shield portion 158 that covers the open end of the interior volume. The first shield portion 154b includes arch-shaped members 164 that are connected to inner and outer base members 166 and 168. Alignment tabs 160b and apertures 162 are also provided.

Here, however, the first shield portion 154b includes antenna guides 188 and antenna guides 190. In the illustrated implementation, each group 174 and 174a includes one or more of the antenna guides 188 and one or more of the antenna guides 190. The spacing between the antenna guides 188 and 190, as well as the spacing between the antenna guides and the inner and outer base members 166 and 168, is such that loop channels 192, 194 and 196 are defined by the first shield portion 154b within the interior volume 156. Although the number of channels may vary, there are three loop channels 192-196 for the three-looped antenna 110. The antenna 110 may be formed by, for example, guiding the inductor assembly 132 between the guides (or between the guides and base members) and around the channels 192-196 while pressing the inductor assembly into the channels. The guides 188 and 190 will then hold the antenna 110 in place and maintain its shape.

Figure 22:
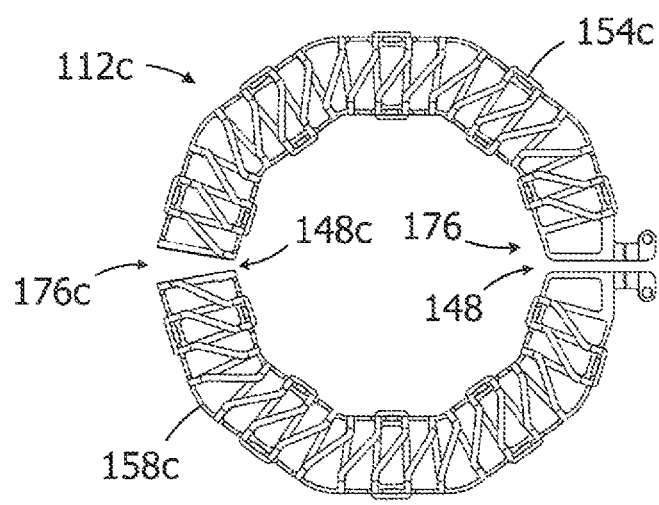
FIG. 22 is a top view of an electromagnetic shield in accordance with one embodiment of a present invention.
Figure 23:
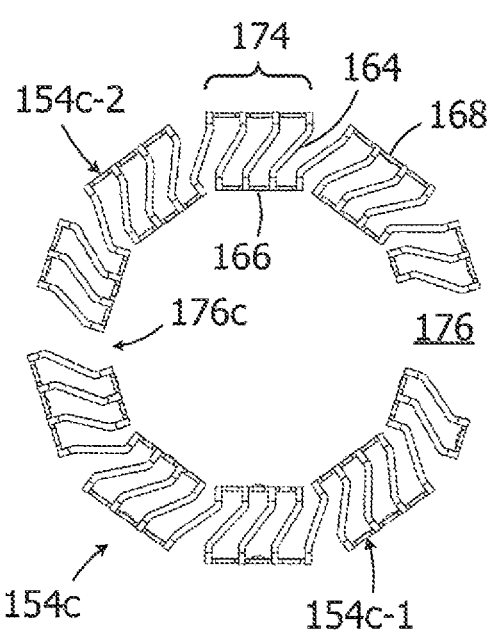
FIG. 23 is a top view of a portion of the electromagnetic shield illustrated in FIG. 18.
Figure 24:
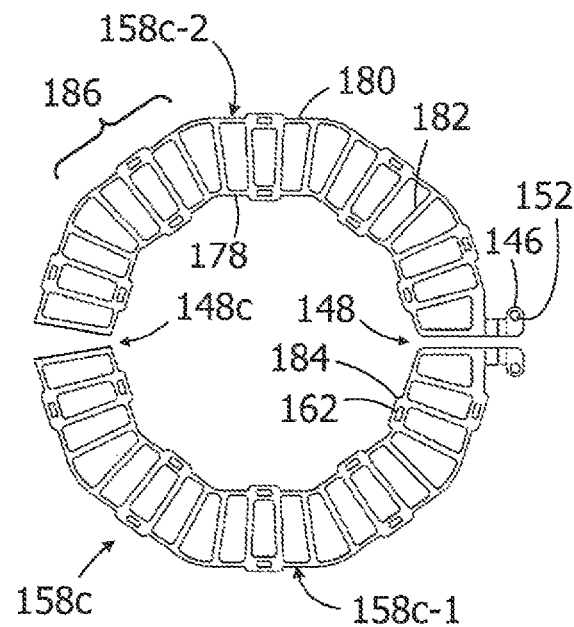
FIG. 24 is a top view of a portion of the electromagnetic shield illustrated in FIG. 22.
Figure 25:
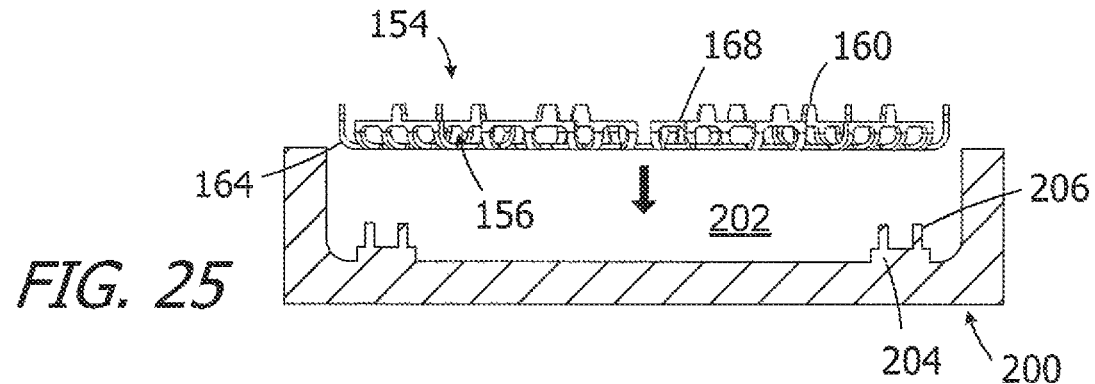
FIGS. 25-30 are partial section views showing respective portions of a method in accordance with one embodiment of a present invention.
Figure 26:
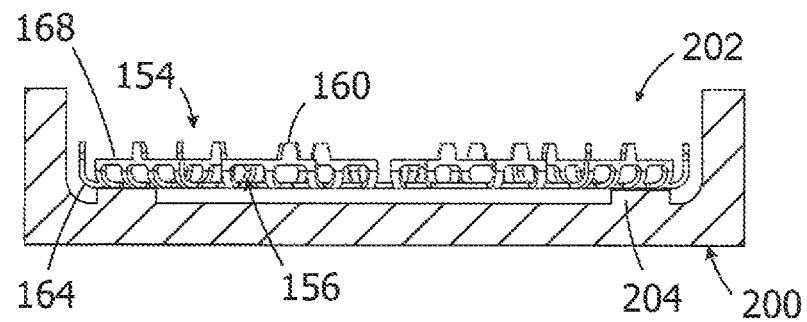
Figure 27:
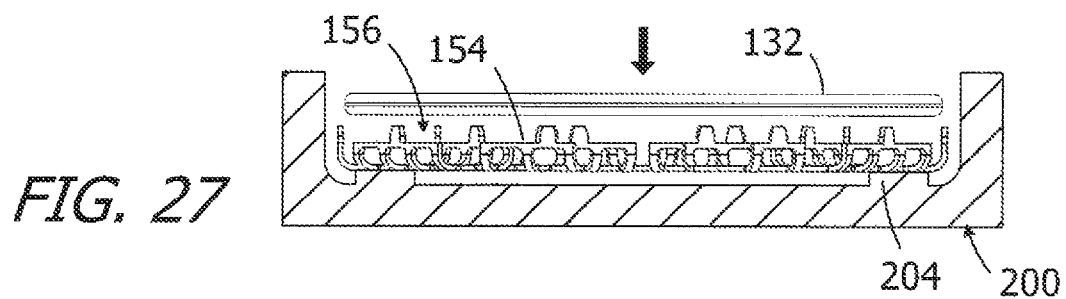

It should also be noted that it may be desirable in some instances to split an electromagnetic shield into two shield parts that are independently connected to the alignment posts 150 (FIG. 6). To that end, and referring to FIGS. 22-24, an electromagnetic shield 112c may be formed from first and second shield portions 154c and 158c. The first shield portion 154c includes parts 154c-1 and 154c-2, while the second shield portion 158c includes parts 158c-1 and 158c-2. The first shield portion parts 154c-1 and 154c-2 are separated by gaps 176 and 176b, while the second shield portion parts 158c-1 and 158c-2 are separated by gaps 148 and 148b. In other implementations, the two shield parts that are disconnected at the gaps 148 and 148c may be connected to a single tab 146, which results in the shield being connected to a single one of the alignment posts 150 (FIG. 6). Alternatively, the electromagnetic shield 112 may be reconfigured such that one of the tabs 146 is omitted, which results in the shield being connected to a single one of the alignment posts 150 (FIG. 6).

With respect to materials and manufacture, suitable materials for the exemplary shield 112 include, but are not limited to, Nitinol and other electrically conductive biocompatible metals such as titanium, gold, and stainless steel. Nitinol is especially useful due to its flexibility and shape memory properties. The first and second shield portions 154 and 158 (as well as the other shield portions described herein) may formed through etching or other suitable fabrication processes. The first shield portion 154 may be initially flat, and then formed into the illustrated three-dimensional shape with a die.

Figure 28:
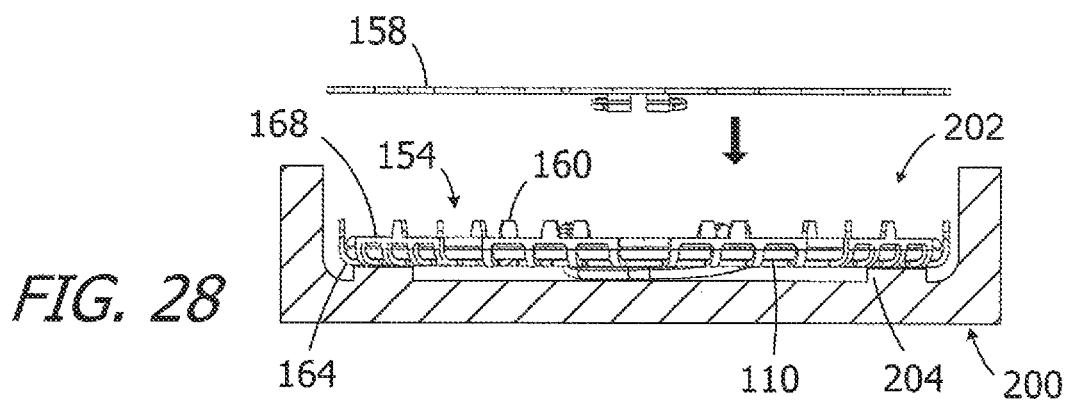
Figure 29:
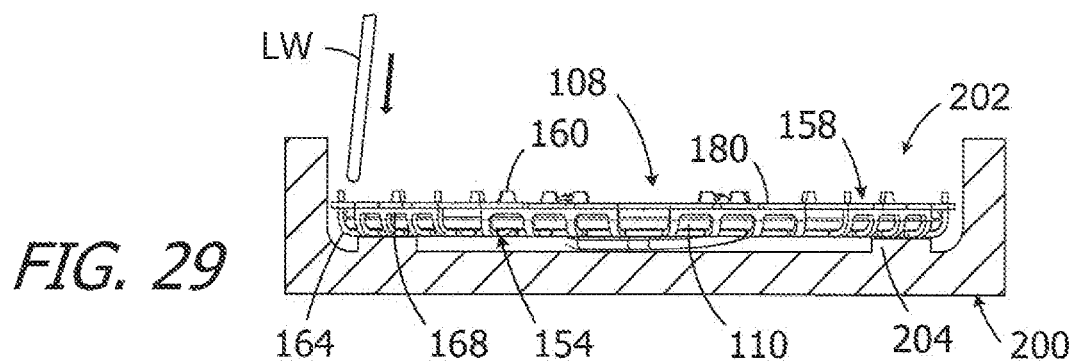

One exemplary method of assembling the exemplary antenna assembly 108 is illustrated in FIGS. 25-29. The first shield portion 154 of the shield 112 is placed into a fixture 200 (FIG. 25) that includes a cavity 202, shield support 204 and antenna guides 206. The fixture 200 is configured to hold the first and second shield portions 154 and 158, as well as the antenna 110, during the assembly process. The open end of the first shield portion interior volume 156 faces upwardly (in the illustrated orientation), as do the tabs 160. When the first shield portion 154 is fully inserted and the arch-shaped members 164 rest on the supports 204 (FIG. 26), the antenna guides 206 will extend through the spaces between the arch-shaped members and into the interior volume 156. The antenna guides 206 together define loop channels (not shown) in a manner similar to that described above with reference to FIGS. 18-21. The inductor assembly 132 may then be pressed into the loop channels (FIG. 27) to form the antenna 110 within the interior volume 156 of the first shield portion 154 (FIG. 28). The antenna 110 is oriented relative to the first shield portion 154 in the manner illustrated in FIGS. 11 and 13. The second shield portion 158 may then be placed onto the first shield portion 154 (FIGS. 28 and 29) in such a manner that the tabs 160 on the first shield portion extend through the apertures 162 on the second shield portion in the manner illustrated in FIG. 6 and align the shield portions with one another. The first and second shield portions 154 and 158 may then be secured to one another to form the shield 112 and complete the antenna assembly 108. For example, a laser welding tool LW (or other welding tool) may be used to bond the first and second shield portions 154 and 158 to one another at one or more of the thickened regions 184 where the tabs 160 pass through the apertures 162 and/or at other regions around the outer perimeter of the shield.

Figure 30:
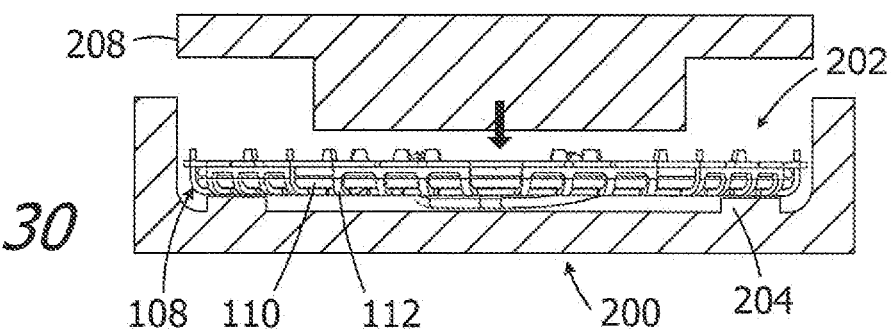
Figure 30A:
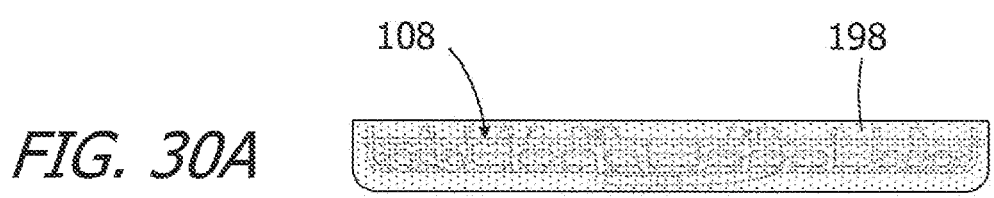
FIG. 30A is an end view of an antenna assembly in accordance with one embodiment of a present invention.

In some instances, in order to ensure that the antenna 110 is maintained in the desired shape after the antenna assembly 108 is removed from the fixture 200, the fixture may also be used as mold. Referring to FIG. 30, a mold cover 208 may be positioned over the cavity 202 and overmold material (e.g., silicone or other suitable materials) may be injected into the cavity to form an overmold 198 (FIG. 30A) over the antenna assembly 108.

Figure 31:
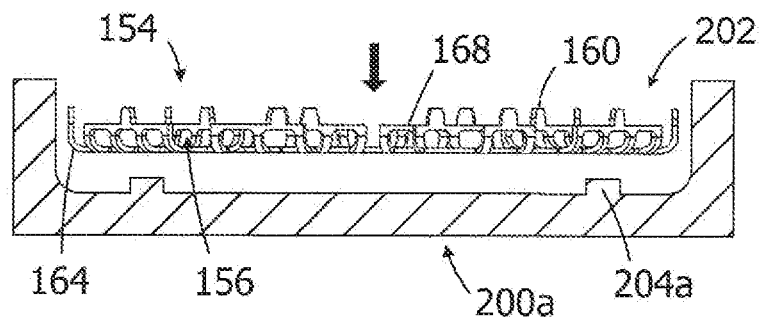
FIGS. 31 and 32 are partial section views showing respective portions of a method in accordance with one embodiment of a present invention.
Figure 32:
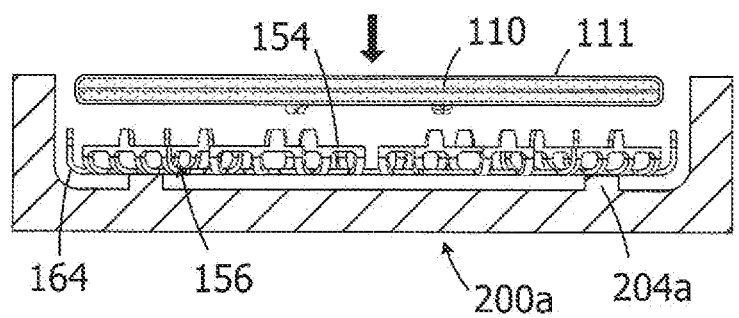

As discussed above with reference to FIG. 10, the exemplary antenna assembly 108 may, but for the free ends of the inductor assembly 132, include an overmolded antenna holder 111 that will maintain the antenna 110 in the desired shape and protect the antenna assembly during storage and subsequent assembly of the cochlear implant 100. Here, the fixture does not need the antenna guides 206, and the fixture 200a (FIG. 31) is identical to the fixture 200 but for the omission of the antenna guides. After the first shield portion 154 has been placed into the fixture 200a, the antenna 110 (with holder 111) may simply be inserted in the and into the interior volume 156 (FIG. 32). The second shield portion 158 may then be positioned on, and secured to, the first shield portion 154 in the manner described above with reference to FIGS. 28 and 29 to complete the antenna assembly.

Figure 33:
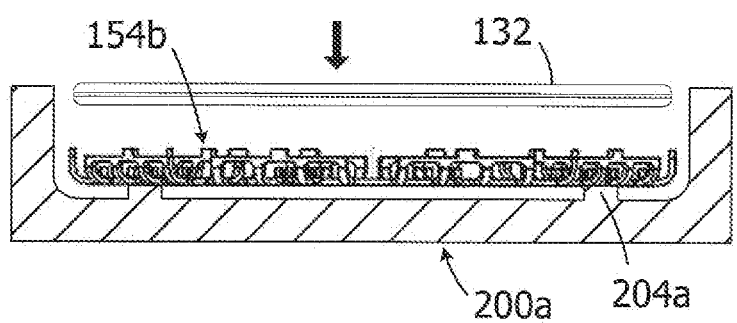
FIGS. 33 and 34 are partial section views showing respective portions of a method in accordance with one embodiment of a present invention.
Figure 34:
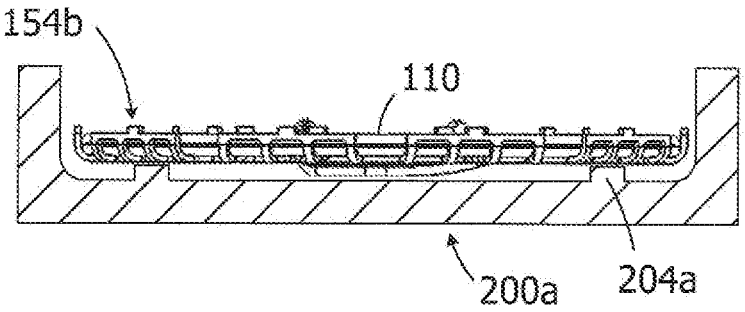

The exemplary shield 112b illustrated in FIGS. 18-21 may be assembled by, for example, placing the shield portion 154b into the fixture 200a and forming the inductor assembly 132 into the antenna 110 using the above described antenna guides 188 and antenna guides 190, as illustrated in FIGS. 33 and 34. The second shield portion 158 may then be positioned on, and secured to, the first shield portion 154 in the manner described above with reference to FIGS. 28 and 29 to complete the antenna assembly. An overmold (not shown) may be formed over the antenna assembly.

Figure 35:
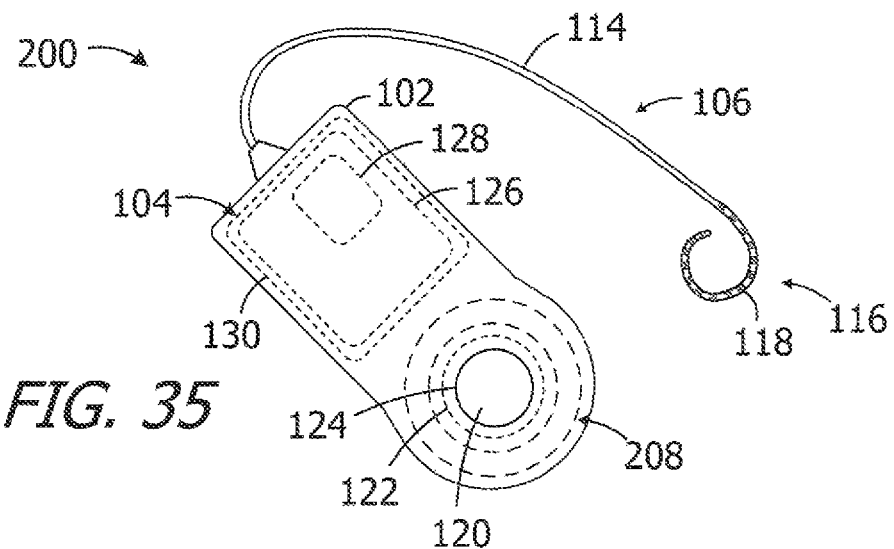
FIG. 35 is a top view of an exemplary implantable cochlear stimulator in accordance with one embodiment of a present invention.
Figure 36:
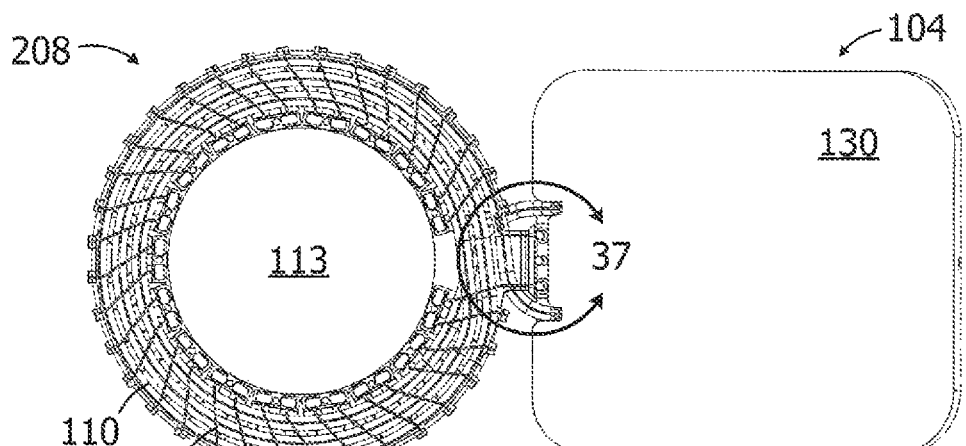
FIG. 36 is a bottom view of a portion of the implantable cochlear stimulator illustrated in FIG. 35.
Figure 37:
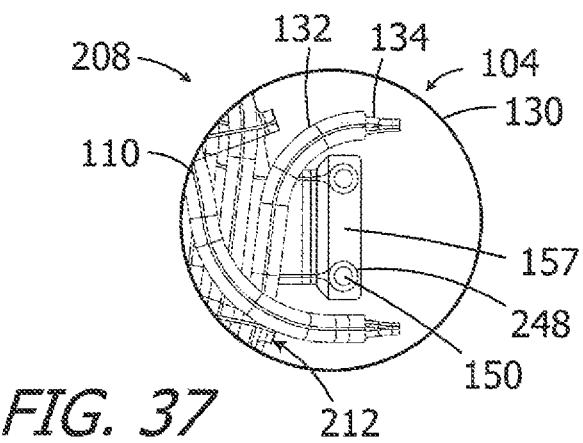
FIG. 37 is an enlarged view of a portion of FIG. 36.

Another exemplary cochlear implant is the cochlear implant 200 illustrated in FIGS. 35-37. The cochlear implant 200 is substantially similar to cochlear implant 100 and similar elements are represented by similar reference numerals. The cochlear implant 200 includes a flexible housing 102 formed from a silicone elastomer or other suitable material, a processor assembly 104, a cochlear lead 106, and an antenna assembly 208 with an antenna coil (or "antenna") 110 and an electromagnetic shield (or "shield") 212. The antenna 110, which is discussed in greater detail above with reference to FIGS. 3-9, may be used to receive data and power by way of an external antenna that is associated with, for example, a sound processor unit, while the electromagnetic shield 212 functions in a manner similar to the electromagnetic shields in other hearing related devices. As discussed above, the cochlear lead 106 may include a flexible body 114, an electrode array 116 at one end of the flexible body, and a plurality of wires (not shown) that extend through the flexible body from the electrodes 118 (e.g., platinum electrodes) in the array 116 to the other end of the flexible body. A positioning magnet 120 is located within a region encircled by the antenna assembly 208 (e.g., within an internal pocket 122 defined by the housing 102). The antenna assembly 208 has an overall annular shape with an open central region 113 to accommodate the magnet 120 and magnet pocket 122. An opening 124 allows the magnet 120 to be removed from the internal pocket 122 if necessary. The exemplary processor assembly 104, which is connected to the electrode array 116 and antenna 110, includes a printed circuit board 126 with a stimulation processor 128 that is located within a hermetically sealed case 130. The case 130 may be formed from titanium or other suitable materials. The stimulation processor 128 converts the stimulation data into stimulation signals that are transmitted to the cochlea by way of the electrodes 118 of the electrode array 116. The exemplary antenna 100a, which is described above with reference to FIGS. 7-9, may also be employed in the antenna assembly 208. In those instances where an antenna 110 (or 110a) will not self-maintain the three concentric loops shape illustrated in FIG. 36 or other desired shape, an overmolded antenna holder 111 (discussed above with reference to FIG. 10) may be employed. The antenna holder 111 will be positioned within the shield 212 along with the antenna 110 (or 110a).

As illustrated in FIG. 37, the exemplary shield 212 includes a pair of conductive rings 248. The conductive rings 248 are welded or otherwise connected to the titanium case 130, and the case is connected to ground circuitry within the case. In the illustrated implementation, the case 130 includes a pair of alignment posts 150 that extend through the conductive rings 248 and orient shield 212 relative to the case.

Figure 38:
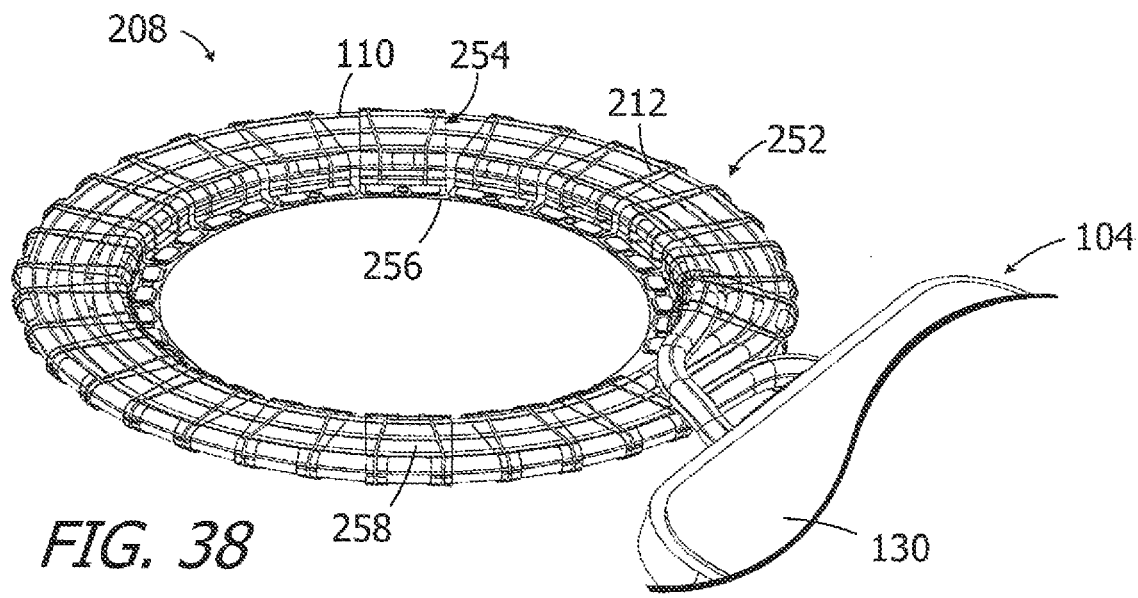
FIG. 38 is a perspective view of a portion of the implantable cochlear stimulator illustrated in FIG. 35.
Figure 39:
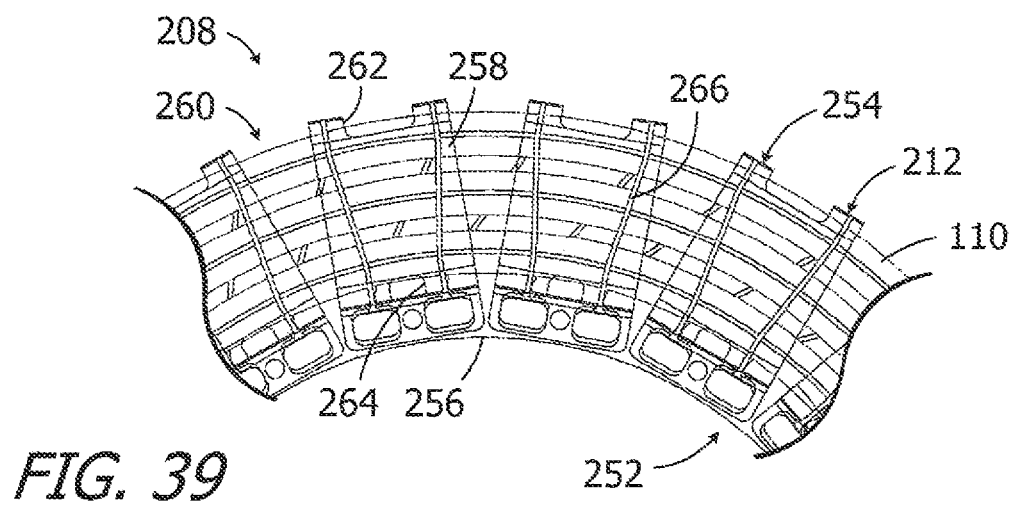
FIG. 39 is a top view of a portion of the implantable cochlear stimulator illustrated in FIG. 35.

As illustrated in FIGS. 38 and 39, the exemplary shield 212 is part of a shield assembly 252 that also includes a flexible, electrically non-conductive shield carrier 254. The shield carrier 254 and the shield 212 may be wrapped around the antenna 110 to form the antenna assembly 208 in the manner described below with reference to FIGS. 40-47.

Turning to FIGS. 40-43, which show the shield assembly 252 in its pre-wrapping, unstressed state, the exemplary shield carrier 254 includes a base member 256, the connector tab 257, and a plurality of separately bendable projections 258 that extend outwardly from base member. In the illustrated implementation, the base member 256 has an annular shape, while the separately bendable projections 258 are separated by gaps 260 and extend radially outwardly from the base member. The shield carrier 254 also includes areas of increased flexibility 262 and 264 (as compared to adjacent portions of the shield carrier) which correspond to locations where the separately bendable projections 258 will be bent as the shield assembly 252 is wrapped around the antenna. The areas of increased flexibility 262 and 264 may be in the form of, for example, apertures (as shown), areas of reduced thickness, chemically treated areas.

Figure 40:
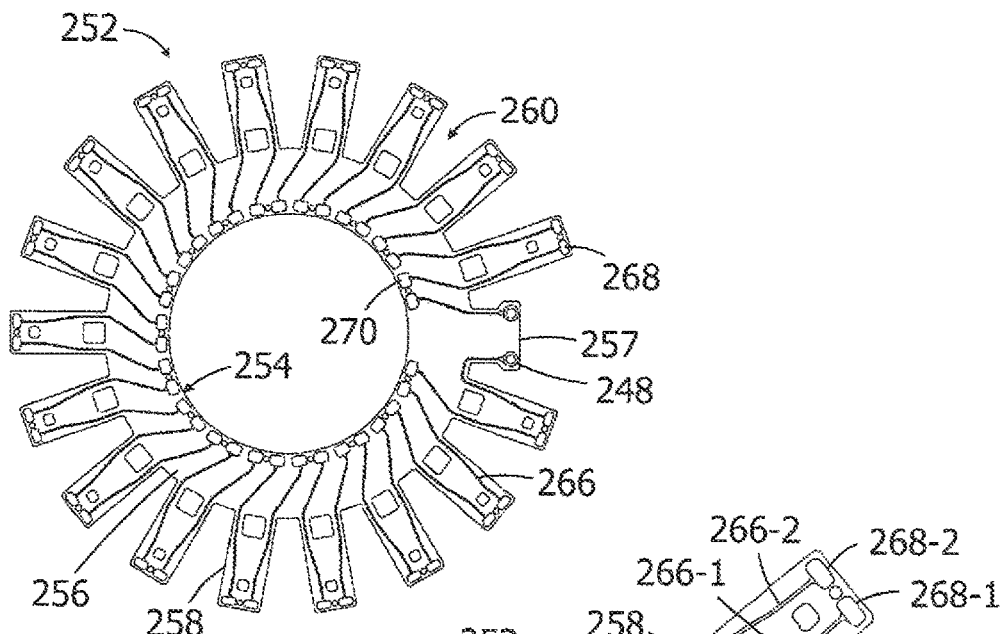
FIG. 40 is a top view of a shield assembly in accordance with one embodiment of a present invention prior to being wrapped around an antenna.
Figure 41:
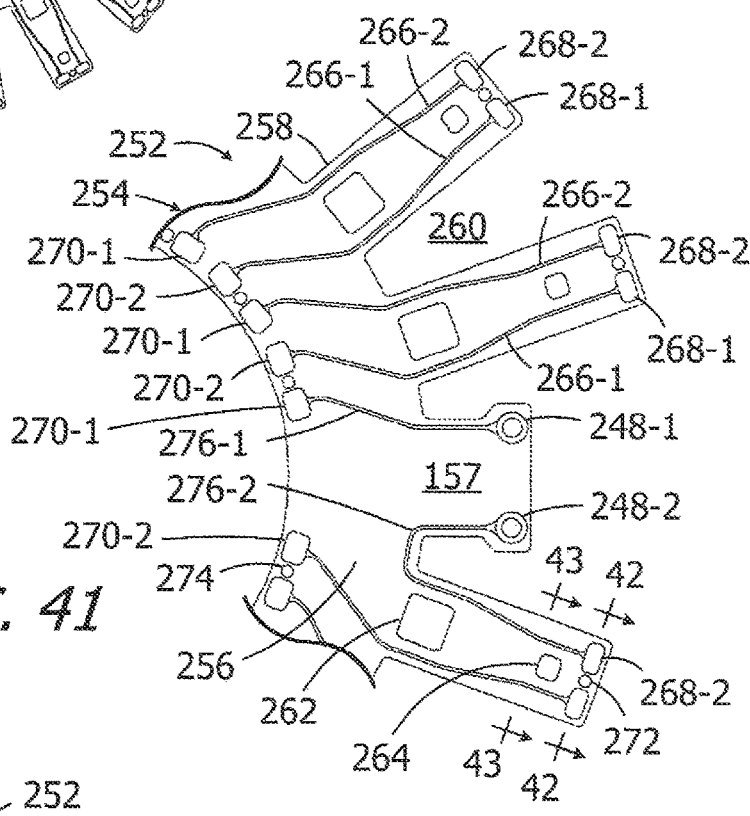
FIG. 41 is an enlarged view of a portion of FIG. 40.
Figure 42:
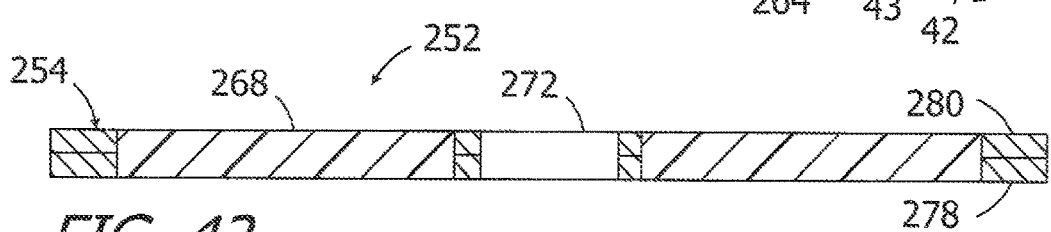
FIG. 42 is a section view taken along line 42-42 in FIG. 41.
Figure 43:
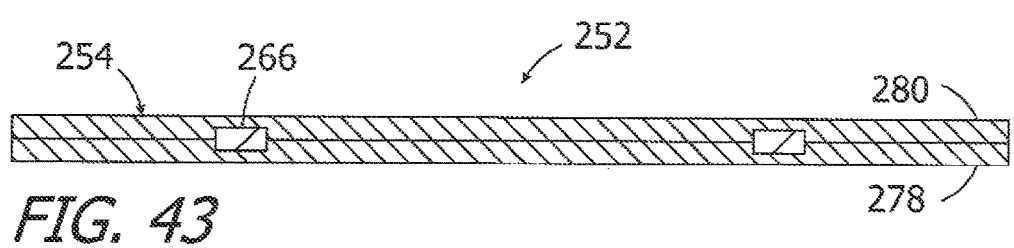
FIG. 43 is a section view taken along line 43-43 in FIG. 41.

The exemplary shield 212 includes a plurality of initially disconnected shield segments 266 that are spaced apart from one another and electrically disconnected from one another when the shield assembly 252 is in the pre-wrapping, unstressed state illustrated in FIGS. 40 and 41. The ends of the shield segments 266 include contact pads 268 and 270. In the illustrated implementation, the separately bendable projections 258 include a pair of shield segments 266-1 and 266-2. The ends of the shield segments 266-1 and 266-2 include contact pads 268-1 and 268-2 as well as contact pads 270-1 and 270-2. As is also discussed below with reference to FIGS. 44 and 45, adjacent shield segments are electrically connected to one another during the assembly process when a contact from one shield segment is brought into contact with, and is welded or otherwise bonded and electrically connected to, a contact from another shield segment. For example, after a separately bendable projection 258 has been bent, the contact pad 268-1 on one shield segment is brought into contact with, and is welded or otherwise bonded and electrically connected to, the contact pad 270-1 from the adjacent shield segment (on the adjacent projection 258), while the contact pad 268-2 on the other shield segment of the bent projection 258 is brought into contact with, and is welded or otherwise bonded and electrically connected to, the contact pad 270-2 from the adjacent shield segment (on the same projection 258). Alignment may be facilitated through the use of alignment apertures 272 and 274 that may be pushed over posts on the assembly fixture.

The conductive rings 248-1 and 248-2 (FIG. 41) on the connector tab 257 may be connected to the shield 212 by way of conductors 276-1 and 276-2 and contact pads 270-1 and 268-2. During the assembly process, the contact pads 270-1 and 268-2 will be respectively connected to contact pads 268-1 and 268-2 of the projections 258 that are located on opposite sides of the connector tab 257.

With respect to manufacture and materials, the exemplary shield carrier 254 may include first and second individual flexible substrate layers 278 and 280 (FIGS. 42 and 43) that are laminated together. The flexible substrate layers 278 and 280 may be formed from flexible biocompatible materials including, but not limited to, polyimides and liquid crystal polymers. The flexible biocompatible material may be transparent (as is shown for explanatory purposes), translucent or opaque. Electrical traces are deposited onto the substrate layer 278 to form the shield segments 266 and conductors 276. The traces may, for example, be formed from a noble metal such as gold or a gold alloy that is deposited using methods such as plating, sputtering, vapor deposition, and shaped using methods such as chemical etching and laser ablation. The traces may also include a thin adhesion layer (e.g., titanium or platinum) that strongly binds with both the polyimide and the noble metal deposited over the adhesion layer. The contact pads 268 and 270 may be vias formed from similar metals that pass through the first and second substrate layers 278 and 280 at the ends of the shield segments. In other implementations, the contact pads 268 and 270 may be part of the electrical traces that are exposed by etching or other suitable processes. It should also be noted that the number of substrate layers, as well as the manner in which the shield is formed, may be adjusted as necessary or desired.

Figure 44:
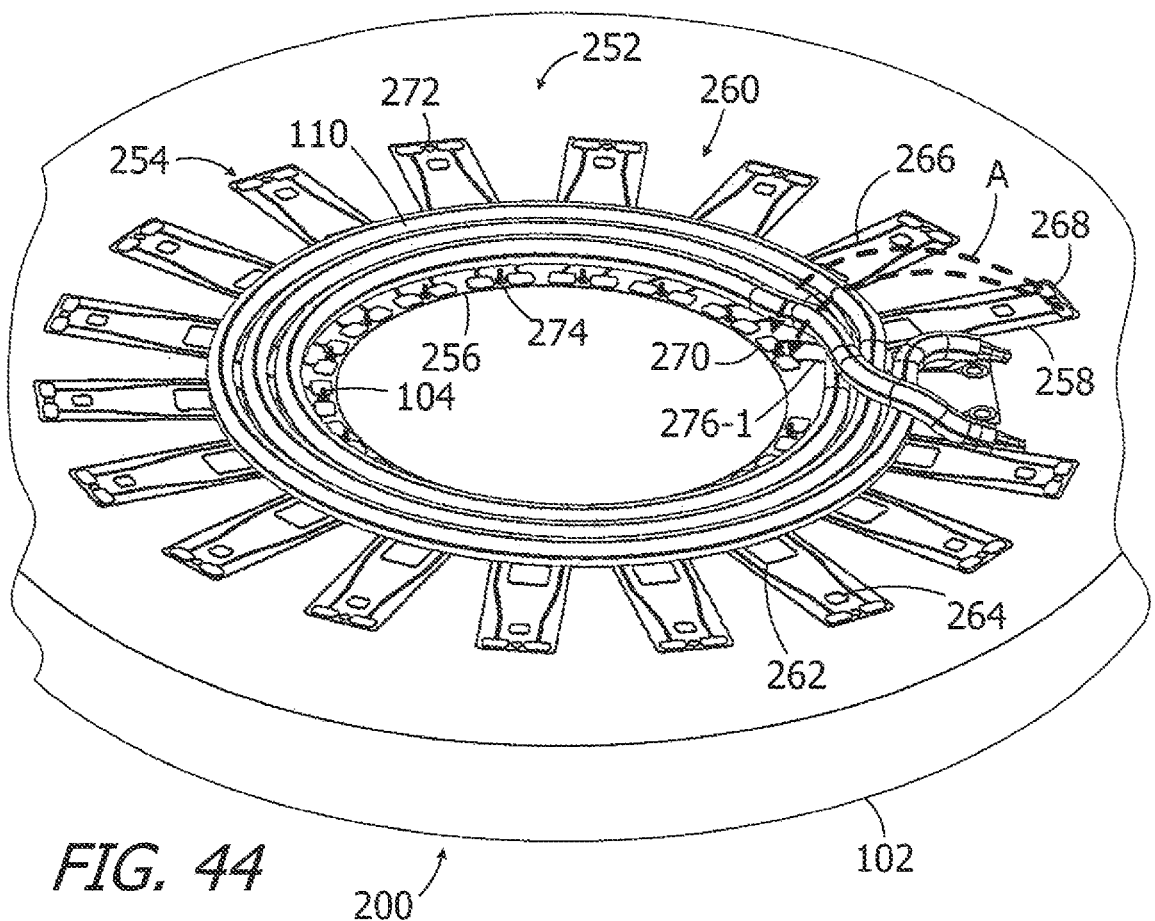
FIG. 44 is a perspective view of a portion of a method in accordance with one embodiment of a present invention.
Figure 45:
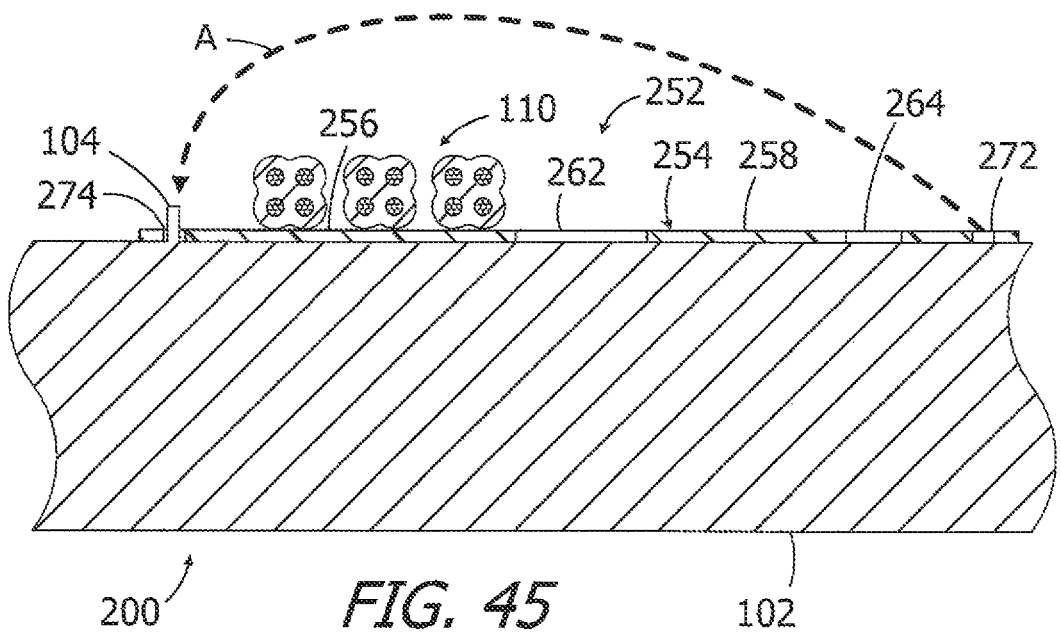
FIG. 45 is a section view of a portion of a method in accordance with one embodiment of a present invention.
Figure 46:
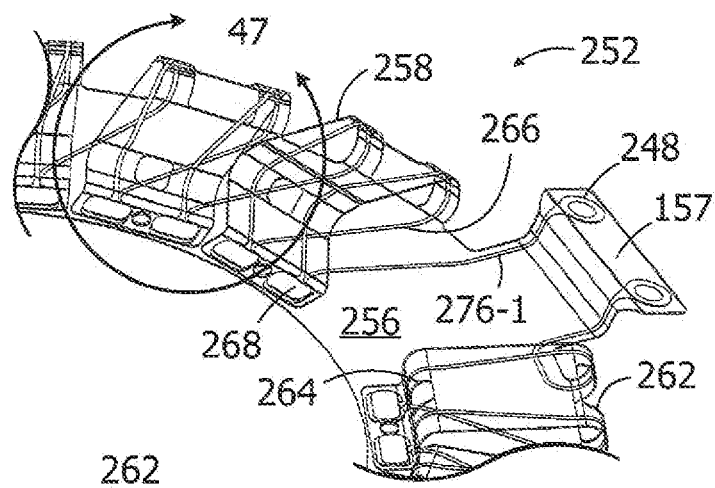
FIG. 46 is a perspective view of a portion of the shield assembly illustrated in FIG. 38.
Figure 47:
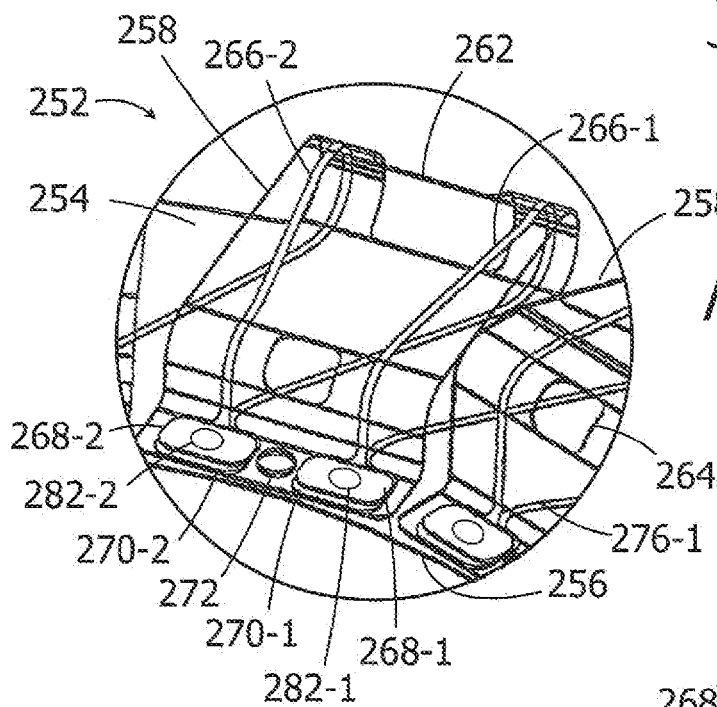
FIG. 47 is an enlarged view of a portion of FIG. 46.

With respect to assembly of the exemplary shield assembly 252, the shield carrier 254, including the shield segments 266 and contacts 268 and 270, may be placed on a fixture, such as the exemplary fixture 200 illustrated in FIGS. 44 and 45. The fixture includes a base 202 and a plurality of posts 204 that extend through the alignment apertures 274. The antenna 110 may be placed onto the shield carrier 254 before or after the shield carrier has been placed on the fixture 200. Each separately bendable projection 258 may then be bent in the direction of arrows A (or "wrapped") around the adjacent portion of the antenna 110 into the wrapped, stressed state illustrated in FIGS. 46 and 47. The antenna 110 is omitted from FIGS. 46 and 47 to facilitate observation of the shield assembly 252. The base 256 and portions of the bendable projections 258 that are located above and below the antenna 110 (in the illustrated orientation) are flat. The areas of increased flexibility 262 and 264 are located at the inner and outer edges of the antenna 110 where the bending primarily occurs. Placing the alignment apertures 272 over the posts 204 aligns the contact pads 268 at one end of the shield segments 266 with the contact pads 270 at the other end to connect the shield segments to one another in series, thereby forming the shield 212. In particular, and referring more specifically to FIG. 47, the contact pad 268-1 on the shield segment 266-1 of a bent projection 258 will be aligned with the contact pad 270-1 from the adjacent shield segment (on the adjacent projection 258), while the contact pad 268-2 on the shield segment 266-2 of the bent projection will be aligned with the contact 270-2 from the adjacent shield segment (on the same projection 258). The aligned contacts 268-1 and 270-1 may be electrically connected to one another through the use of methods such as, for example, welding (resistance or laser) and gold bond ball bonding. A weld 282-1 is employed in the illustrated implementation. The aligned contacts 268-2 and 270-2 are electrically connected with a weld 282-2. This process may be repeated for each of the bendable projections 258 to complete the shield 212 and to connect the shield to the conductive rings 248.

Figure 48:
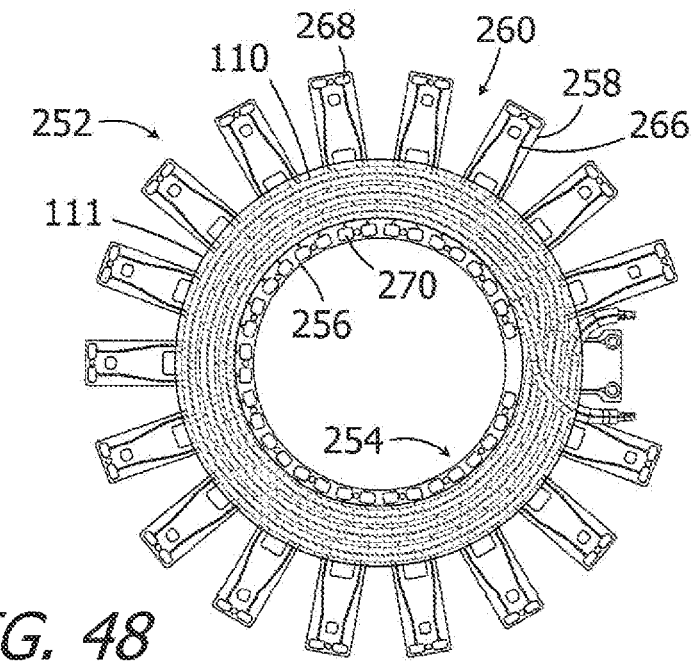
FIG. 48 is a top view of an antenna assembly in accordance with one embodiment of a present invention in an unassembled state.

As discussed above with reference to FIG. 10, an overmolded antenna holder 111 may be used to maintain the antenna 110 in the desired shape. Here, the antenna 110 (with holder 111) may be placed onto the shield carrier 254 in the manner illustrated in FIG. 48. The shield 212 may then be formed in manner described above with reference to FIGS. 44-47.

Figure 49:
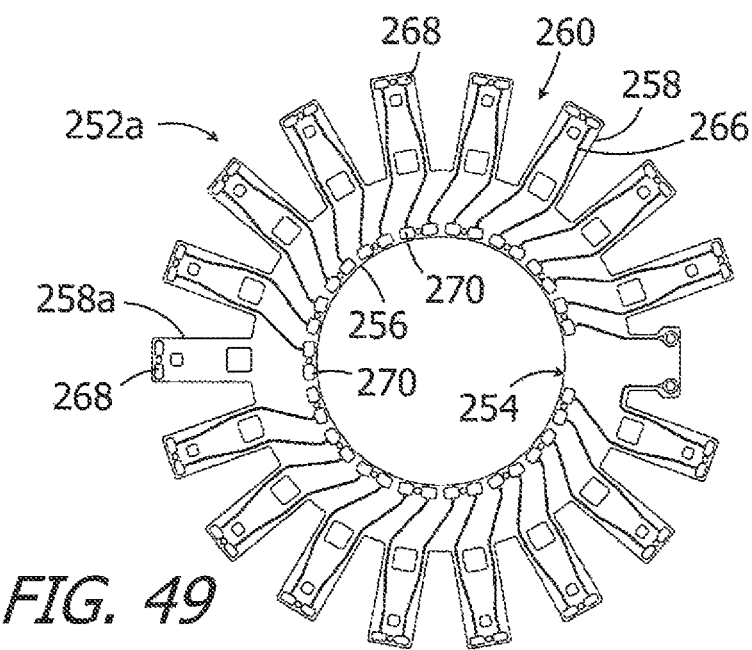
FIG. 49 is a top view of a shield assembly in accordance with one embodiment of a present invention prior to being wrapped around an antenna.

It should also be noted that it may be desirable in some instances to split an electromagnetic shield 212 into two shield parts that are independently connected to the alignment posts 150 (FIG. 37). Such separation may be accomplished in a number of ways. For example, and referring to FIG. 49, the exemplary shield assembly 252a is substantially similar to the shield assembly 252 and similar elements are represented by similar reference numerals. For example, the shield assembly 252a includes a shield carrier 254, with a base member 256 and a plurality of separately bendable projections 258, and a plurality of initially disconnected shield segments 266 with contact pads 268 and 270. Here, however, the bendable segment 258a does not include shield segments 266. As a result, when the bending and welding process described above is complete (including the bendable segment 258a and associated contact pads 268 and 270), the resulting shield will have two portions that are disconnected at the bendable segment 258a. Alternatively, one of the bendable segments 258, as well as the associated shield segments 266 and contact pads 268 and 270, may simply be omitted. In other implementations, the two portions that are disconnected at the bendable segment 258a may be connected to the same conductive ring (e.g., conductive ring 248-1 in FIG. 41), which results in the shield being connected to a single one of the alignment posts 150 (FIG. 37). Alternatively, the shield assembly 252 may be reconfigured such that one of the conductive rings 248 is omitted (e.g., conductive ring 248-1 in FIG. 41), which results in the shield being connected to a single one of the alignment posts 150 (FIG. 37).

Figure 50:
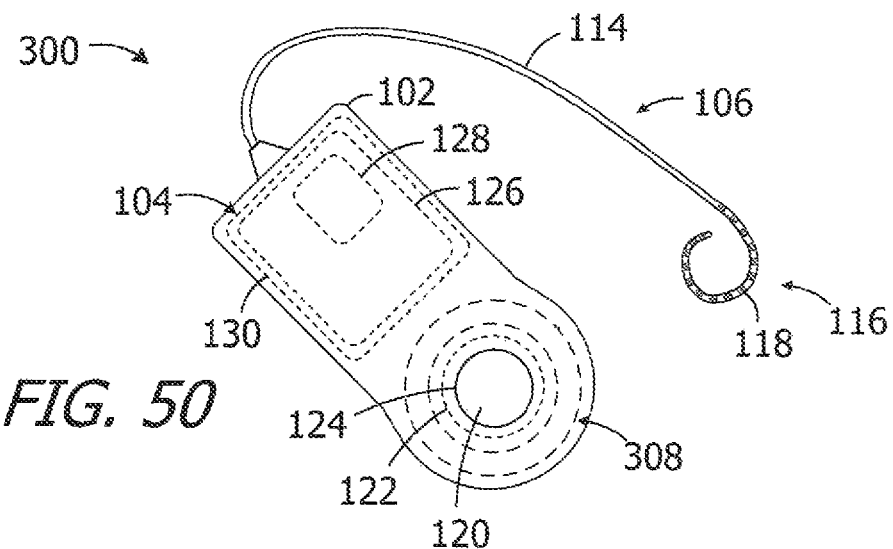
FIG. 50 is a top view of an exemplary implantable cochlear stimulator in accordance with one embodiment of a present invention.
Figure 51:
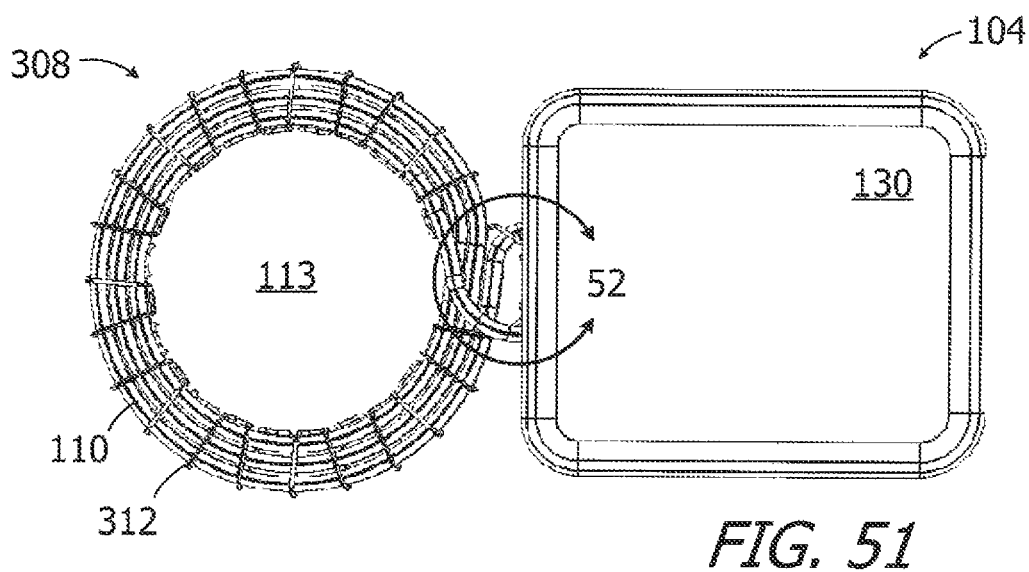
FIG. 51 is a bottom view of a portion of the implantable cochlear stimulator illustrated in FIG. 50.
Figure 52:
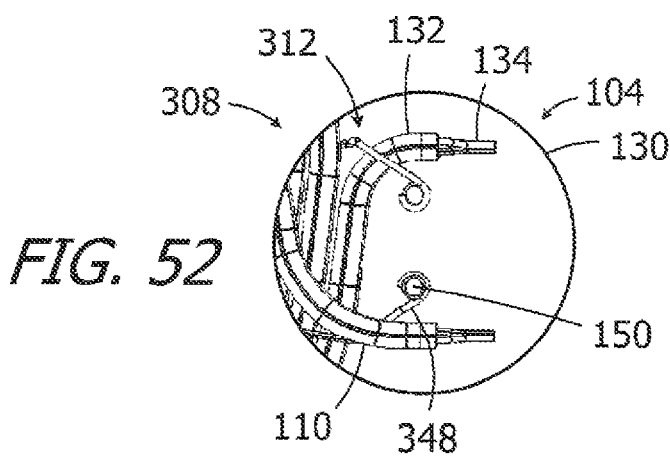
FIG. 52 is an enlarged view of a portion of FIG. 51.

Another exemplary cochlear implant is the cochlear implant 300 illustrated in FIGS. 50-52. The cochlear implant 300 is substantially similar to cochlear implant 100 and similar elements are represented by similar reference numerals. The cochlear implant 300 includes a flexible housing 102 formed from a silicone elastomer or other suitable material, a processor assembly 104, a cochlear lead 106, and an antenna assembly 308 with an antenna coil (or "antenna") 110 and an electromagnetic shield (or "shield") 312. The antenna 110, which is discussed in greater detail above with reference to FIGS. 3-9, may be used to receive data and power by way of an external antenna that is associated with, for example, a sound processor unit, while the electromagnetic shield 312 functions in a manner similar to the electromagnetic shields in other hearing related devices. As discussed above, the cochlear lead 106 may include a flexible body 114, an electrode array 116 at one end of the flexible body, and a plurality of wires (not shown) that extend through the flexible body from the electrodes 118 (e.g., platinum electrodes) in the array 116 to the other end of the flexible body. A positioning magnet 120 is located within a region encircled by the antenna assembly 308 (e.g., within an internal pocket 122 defined by the housing 102). The antenna assembly 308 has an overall annular shape with an open central region 113 to accommodate the magnet 120 and magnet pocket 122. An opening 124 allows the magnet 120 to be removed from the internal pocket 122 if necessary. The exemplary processor assembly 104, which is connected to the electrode array 116 and antenna 110, includes a printed circuit board 126 with a stimulation processor 128 that is located within a hermetically sealed case 130. The case 130 may be formed from titanium or other suitable materials. The stimulation processor 128 converts the stimulation data into stimulation signals that are transmitted to the cochlea by way of the electrodes 118 of the electrode array 116. The exemplary antenna 100a, which is described above with reference to FIGS. 7-9, may also be employed in the antenna assembly 308. In those instances where an antenna 110 (or 110a) will not self-maintain the three concentric loops shape illustrated in FIG. 36 or other desired shape, an overmolded antenna holder 111 (discussed above with reference to FIG. 10) may be employed. The antenna holder 111 will be positioned within the shield 312 along with the antenna 110 (or 110a).

As illustrated in FIG. 52, the exemplary shield 312 includes a pair of conductive curved ends 348, which may be formed before or during the assembly process. The curved ends 348 are welded or otherwise connected to the titanium case 130, and the case is connected to ground circuitry within the case. In the illustrated implementation, the case 130 includes a pair of alignment posts 150 that extend through the curved ends 348 and orient shield 312 relative to the case. It should also be noted that the curved ends 348 in the illustrated embodiment are at the free ends of a continuous wire (or other elongate structure), which results in a shield 312 that can be held and/or manipulated from the ends thereof during assembly, as opposed to completely closed circle.

Figure 53:
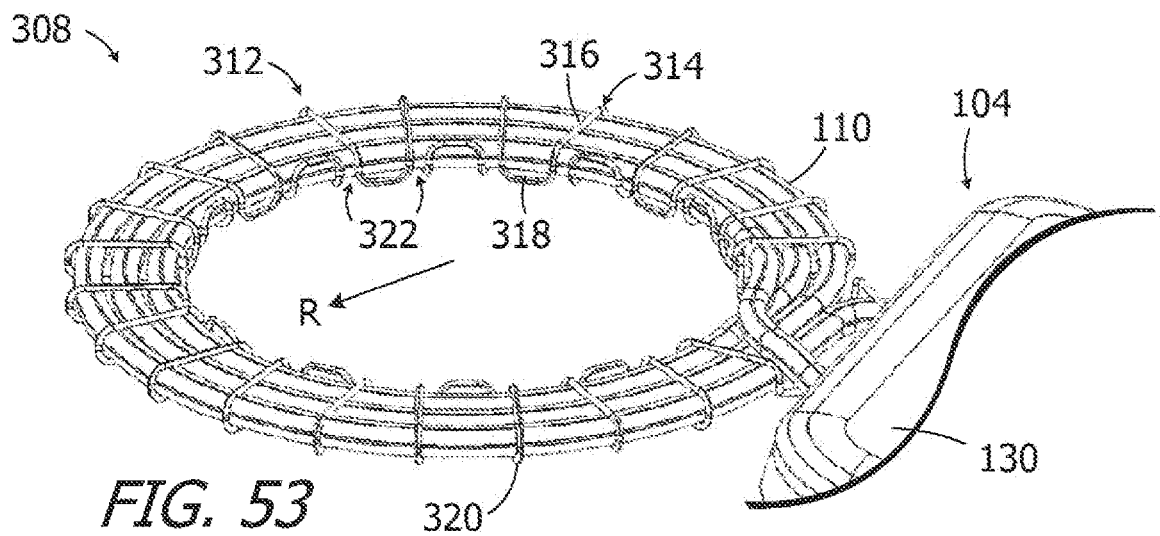
FIG. 53 is a perspective view of a portion of the implantable cochlear stimulator illustrated in FIG. 50.
Figure 54:
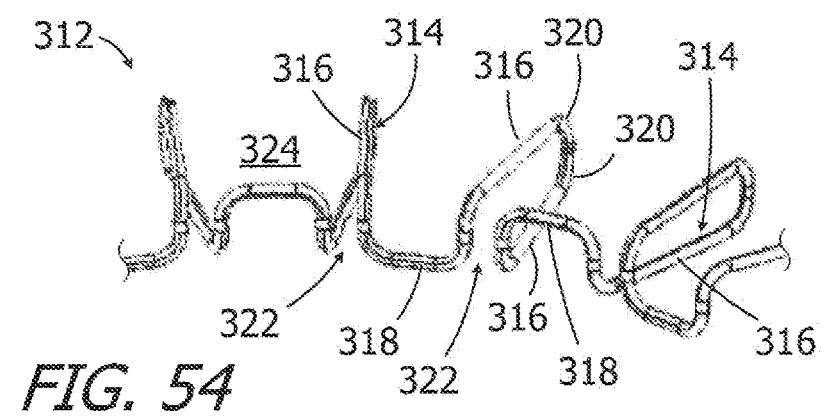
FIG. 54 is a perspective view of a portion of the implantable cochlear stimulator illustrated in FIG. 50.
Figure 55:
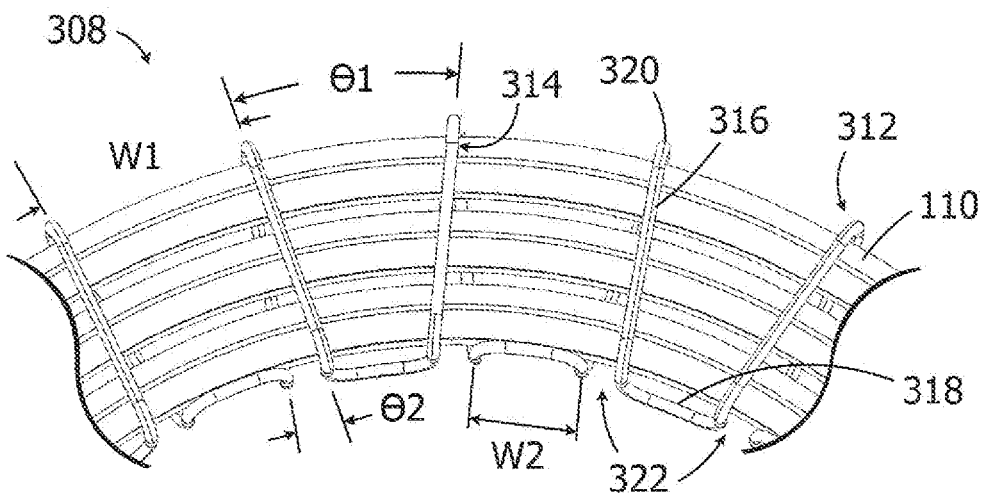
FIG. 55 is a top view of a portion of the implantable cochlear stimulator illustrated in FIG. 50.
Figure 56:
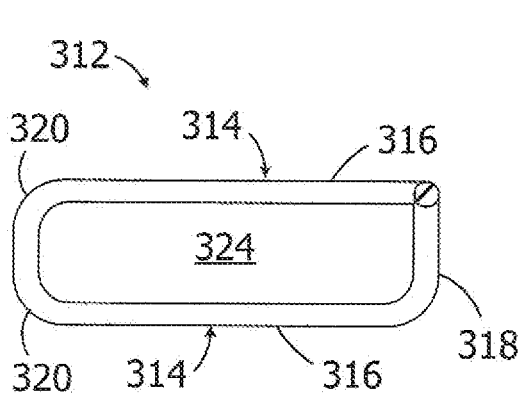
FIGS. 56-59 are section views showing respective portions of methods in accordance with embodiment of present inventions.
Figure 59:
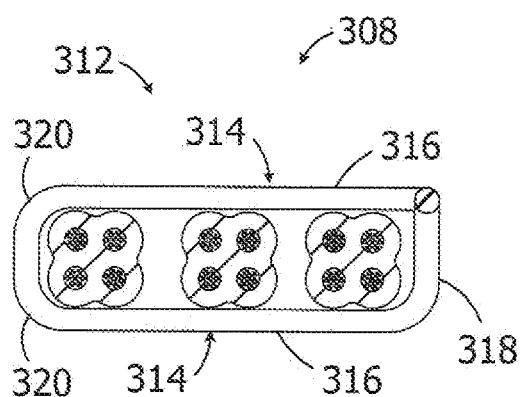

Turning to FIGS. 53-55, the exemplary shield 312 has an overall annular shape and is configured in such a manner that it does not form a continuous loop around the antenna 110 (or 110a). As used herein, a shield that does not form a continuous loop around an antenna (i.e., forms a "discontinuous loop around the antenna") is a shield that follows an uninterrupted path, without reversal of direction, a plurality of times around the antenna. For example, a shield wire that is wound repeatedly around an antenna will form a continuous somewhat helical shape around the antenna. When formed from a resilient material (e.g., a wire formed from a super-elastic material such as Nitinol or a less elastic resilient material), the discontinuity of the present discontinuous loop results in an openable shield that may be provided pre-set in its final shape, then deformed in such a manner that the antenna can be inserted into the shield through an opening enlarged by the deformation (of a size sufficient to receive the antenna), and then released from the deforming force whereby the resilience of the shield will return the shield to its pre-set shape.

In the exemplary implementation illustrated in FIGS. 53-55, the shield 312 includes a plurality of shield portions 314, each of which includes a pair of elongate members 316 that are connected to one another by an inner perimeter portion 318 (e.g., the illustrated U-shaped inner perimeter portion 318). The inner perimeter portions 318, which are perpendicular to the elongate member 316, together define the inner perimeter of the shield 312. The shield portions 314 also include outer perimeter portions 320 (e.g., the illustrated curved outer perimeter portions 320) that define the outer perimeter of the shield 312. Adjacent shield portions 314 are connected to one another in series by their respective outer perimeter portions 320. With reference to the associated antenna 110, the elongate members 316 extend generally in the radial direction R, the U-shaped inner perimeter portions 318 extend generally in directions that are tangential to the inner peripheral surface of the antenna 110, and the outer perimeter portions 320 extend around the outer peripheral surface of the antenna. The elongate members 316 of adjacent shield portions 314 are located on opposite sides of the antenna 110. The U-shaped inner perimeter portions 318 of adjacent shield portions 314 extend in opposite directions and are spaced apart from one another with gaps 322 therebetween. Put another way, the orientation of each shield portion 314 is the opposite of the orientation of the adjacent shield portions.

The gaps 322 between adjacent shield portions 314 in the illustrated embodiment together define an undulating opening that extends along the inner perimeter of the shield 312. The interior volume 324 for the antenna 110 is defined by the shield portions 314. Additionally, as noted above, the shield 312 may be formed from Nitinol (e.g., Nitinol wire), other super-elastic materials (including wires formed therefrom), or other resilient materials such as DFT or stainless steel wire that resist plastic deformation when the shield is stretched in the manner described below. In addition to the above described shape memory benefits, the use of super-elastic material improves the impact resistance of the shield.

With respect to the dimensions of the exemplary shield 312, which has an inner diameter of about 19.0 mm and an outer diameter of about 27.0 mm, the shield portions 314 have an outer perimeter width W1 of about 3.5 mm (FIG. 55) and an inner perimeter width of about 1.8 mm. The angle θ1 defined by the elongate members 316 of the same shield portion 314 is about 25° and the angle θ2 between the elongate members 316 of adjacent shield portions 314 is about 10°. As used herein, the word about means±10%.

Figure 57:
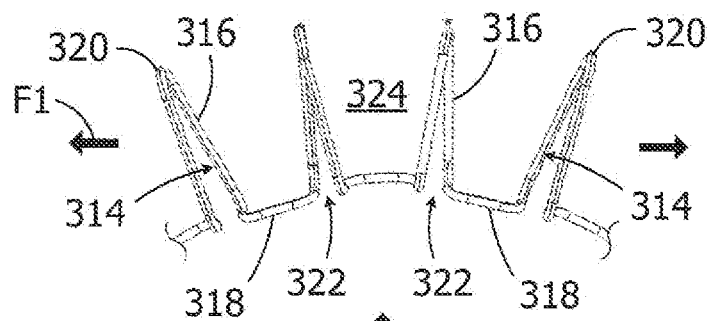
Figure 58:
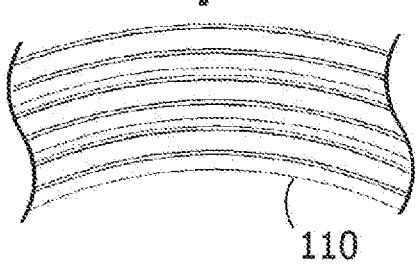

The antenna assembly 308 may be assembled in, for example the manner illustrated in FIGS. 56-59. The shield 312 is shown in its pre-set shape in FIGS. 56 and 57. Forces F1 may be applied to some or all of the shield 312 to stretch the shield (or a portion thereof) out of its pre-set shape and increase the distance between adjacent shield portions 314. In particular, the space between adjacent inner perimeter portions 318 is increased, thereby increasing the size of the gaps 322. Alternatively, or in addition, forces F2 may be applied in the manner illustrated in FIG. 58 to stretch the shield out of its pre-set shape and increase the distance between adjacent shield portions 314 and, in particular, between inner perimeter portions 318, thereby increasing the size of the gaps 322. Once the shield 312 has been manipulated out of its pre-set shape, the antenna 110 may be inserted into the interior volume 224 through the now larger gaps 322 that together defining an opening that is coextensive with the inner perimeter of the shield (FIGS. 57 and 58). The forces (e.g., forces F1 and/or F2) may then be removed to allow the shield to return to its pre-set shape. For example, different portions of the shield may be serially manipulated out of the pre-set shape, as different portions of the antenna 110 are serially inserted into the interior volume 224 through the now larger gaps 322, and then allowed to return to the pre-set shape. This process may continue until the antenna 110 is entirely within the shield 312 in the manner illustrated in FIGS. 53 and 59.

It should also be noted that, in other implementations, the shield may be provided with an opening for the antenna in places other than the inner perimeter. For example, the configuration of the shield may be such that the opening for the antenna is located along the outer perimeter or is located between the inner and outer perimeters.

Figure 60:
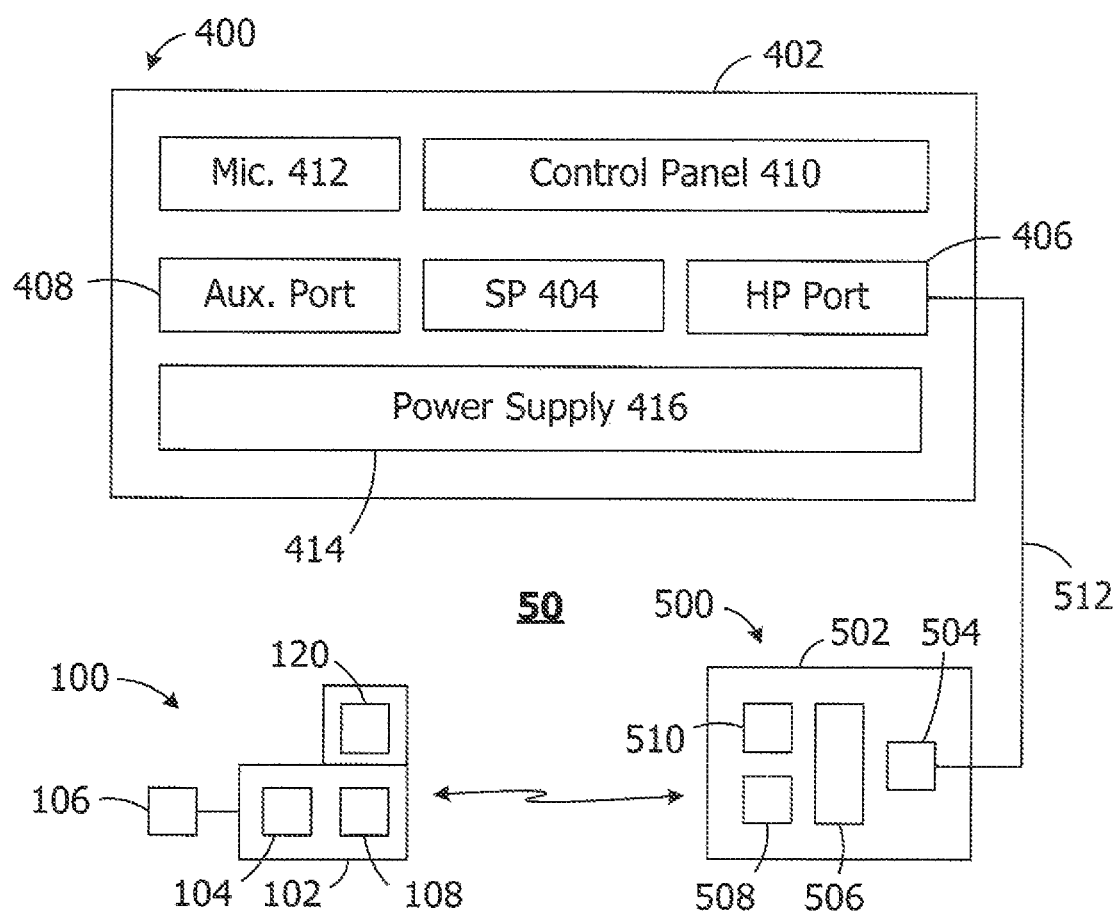
FIG. 60 is a diagrammatic view of an exemplary ICS system.

The present inventions have application in a wide variety of systems including, but not limited to, those that provide sound (i.e., either sound or a perception of sound) to the hearing impaired. One example of such a system is an ICS system where an external sound processor communicates with a cochlear implant. Turning to FIG. 60, the exemplary cochlear implant system 50 includes the cochlear implant 100 (or 200 or 300), a sound processor, such as the illustrated body worn sound processor 400 or a behind-the-ear sound processor, and a headpiece 500.

As noted above with reference to FIG. 1, the exemplary cochlear stimulator 100 illustrated in FIG. 60 includes a flexible housing 102 formed from a silicone elastomer or other suitable material, a processor assembly 104, a cochlear lead 106 with an electrode array, an antenna assembly 108, and a positioning element 120.

The exemplary body worn sound processor 400 includes a housing 402 in which and/or on which various components are supported. Such components may include, but are not limited to, sound processor circuitry 404, a headpiece port 406, an auxiliary device port 408 for an auxiliary device such as a mobile phone or a music player, a control panel 410, one or more microphones 412, and a power supply receptacle 414 for a removable battery or other removable power supply 416 (e.g., rechargeable and disposable batteries or other electrochemical cells). The sound processor circuitry 404 converts electrical signals from the microphone 412 into stimulation data. The exemplary headpiece 500 includes a housing 502 and various components, e.g., a RF connector 504, a microphone 506, an antenna (or other transmitter) 508 and a disk-shaped positioning magnet 510, that are carried by the housing. The headpiece 500 may be connected to the sound processor headpiece port 406 by a cable 512. The positioning magnet 510 is attracted to the magnet 120 of the cochlear stimulator 100, thereby aligning the antenna 508 with the antenna of the antenna assembly 108.

The stimulation data and, in many instances power, is supplied to the headpiece 500. The headpiece 500 transcutaneously transmits the stimulation data, and in many instances power, to the cochlear implant 100 by way of a wireless link between the antennas. The stimulation processor 128 (FIG. 1) converts the stimulation data into stimulation signals that stimulate the electrodes of the electrode array on the cochlear lead 106.

In at least some implementations, the cable 512 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 412 on the sound processor 400, the microphone 506 may be also be omitted in some instances. The functionality of the sound processor 400 and headpiece 500 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. By way of example, the inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:
1. An antenna assembly for use with a medical implant, the antenna assembly comprising:
an antenna that defines at least one turn; and
an electromagnetic shield assembly including
an electrically non-conductive flexible shield carrier, and
an electromagnetic shield carried by the flexible shield carrier
wherein the electromagnetic shield assembly is wrapped around the antenna in such a manner that the shield carrier includes a first portion on a first side of the antenna, a second portion on a second side of the antenna that is opposite the first side and a bent portion that extends from the first portion to the second portion.

2. An antenna assembly as claimed in claim 1, wherein the electromagnetic shield comprises a plurality of shield members including first and second ends and first and second contact pads at the first and second ends.

3. An antenna assembly as claimed in claim 2, wherein the first contact pads are located on the separately bendable projections and the second contact pads are located on the base member.

4. An antenna assembly as claimed in claim 3, wherein the shield members are arranged such that the first contact pad on a first separately bendable projection is in contact with the second contact pad of a second separately bendable projection that is adjacent to the first separately bendable projection.

5. An antenna assembly as claimed in claim 1, wherein the shield carrier is formed from at least one of a polyimide and a liquid crystal polymer.

6. An antenna assembly as claimed in claim 1, wherein the antenna includes a conductor and an electrically non-conductive carrier defining a lumen in which the conductor is located.

7. An antenna assembly as claimed in claim 1, wherein the antenna is located within an overmolded antenna holder.

8. An antenna assembly as claimed in claim 1, wherein the electromagnetic shield includes a first portion on the first side of the antenna, a second portion on the second side of the antenna and a bent portion that extends from the first portion to the second portion.

9. A cochlear implant, comprising:
a stimulation processor;
a cochlear lead with an electrode array operably connected to the stimulation processor; and
an antenna assembly as claimed in claim 1 operably connected to the stimulation processor.

10. An antenna assembly for use with a medical implant, the antenna assembly comprising:
an antenna that defines at least one turn; and
an electromagnetic shield assembly wrapped around antenna and including
an electrically non-conductive flexible shield carrier that includes a base member and a plurality of separately bendable projections that extend outwardly from base member such that adjacent separately bendable projections are separated from one another by gaps and are wrapped around respective adjacent portions of the antenna, and
an electromagnetic shield carried by the flexible shield carrier.

11. An antenna assembly as claimed in claim 10, wherein the base member comprises an annular base member.

12. An antenna assembly as claimed in claim 10, wherein the separately bendable projections extend radially from the base member.

13. An antenna assembly as claimed in claim 10, wherein the separately bendable projections include at least one area of increased flexibility.

14. An antenna assembly as claimed in claim 10, wherein the base member and the separately bendable projections include alignment apertures.

15. An antenna assembly for use with a medical implant, the antenna assembly comprising:
an antenna, defining at least one turn, with a conductor that includes a plurality of twisted wires and an electrically non-conductive carrier defining a lumen in which the conductor is located; and
an electromagnetic shield assembly wrapped around antenna and including
an electrically non-conductive flexible shield carrier, and
an electromagnetic shield carried by the flexible shield carrier.

16. An antenna assembly for use with a medical implant, the antenna assembly comprising:
an antenna, defining at least one turn, with a plurality of conductors and an electrically non-conductive carrier defining a plurality of lumens in which the plurality of conductors are respectively located; and
an electromagnetic shield assembly wrapped around antenna and including
an electrically non-conductive flexible shield carrier, and
an electromagnetic shield carried by the flexible shield carrier.

* * * * *